US011147469B2

(12) United States Patent
Sidar et al.

(10) Patent No.: US 11,147,469 B2
(45) Date of Patent: *Oct. 19, 2021

(54) SYSTEM FOR DETECTING THE LOCATION OF AN ENDOSCOPIC DEVICE DURING A MEDICAL PROCEDURE

(71) Applicant: EndoChoice, Inc., Alpharetta, GA (US)

(72) Inventors: Itay Sidar, Haifa (IL); Idan Levy, Hadera (IL); Lior Mor, Haifa (IL)

(73) Assignee: EndoChoice, Inc., Alpharetta, GA (US)

( * ) Notice: Subject to any disclaimer, the term of this patent is extended or adjusted under 35 U.S.C. 154(b) by 92 days.

This patent is subject to a terminal disclaimer.

(21) Appl. No.: 16/455,191

(22) Filed: Jun. 27, 2019

(65) Prior Publication Data
US 2019/0380616 A1 Dec. 19, 2019

Related U.S. Application Data

(63) Continuation of application No. 15/045,590, filed on Feb. 17, 2016, now Pat. No. 10,376,181.
(Continued)

(51) Int. Cl.
A61B 1/00 (2006.01)
A61B 90/96 (2016.01)
(Continued)

(52) U.S. Cl.
CPC ............ A61B 5/065 (2013.01); A61B 1/0005 (2013.01); A61B 1/00154 (2013.01); A61B 1/01 (2013.01);
(Continued)

(58) Field of Classification Search
CPC ... A61B 5/065; A61B 1/0005; A61B 1/00154; A61B 1/01; A61B 34/20;
(Continued)

(56) References Cited

U.S. PATENT DOCUMENTS 3,639,714 A 2/1972 Fujimoto
3,955,064 A 5/1976 Demetrio
(Continued)

FOREIGN PATENT DOCUMENTS

CA 2297986 3/1999
CA 2765559 12/2010
(Continued)

OTHER PUBLICATIONS

Office Action dated Jun. 30, 2016 for U.S. Appl. No. 13/655,120.
(Continued)

Primary Examiner — Timothy J Neal
Assistant Examiner — William B Chou
(74) Attorney, Agent, or Firm — Bookoff McAndrews, PLLC

(57) ABSTRACT

A system for detecting the location of an endoscopic device inside a patients' body comprises an endoscope assembly with an insertion tube having a set of codes indicative of an insertion depth and a rotational direction of the endoscopic device and a detector to detect the set of codes and calculate the location information. The images captured by the endoscopic device are automatically tagged with corresponding location information. Optionally, the endoscope assembly further comprises a system for generating three dimensional images and videos without increasing the number of cameras. Optionally, the endoscope assembly further comprises a system having a plurality of sensor devices for generating a real time image map of an endoscopic tip portion traversing a lumen. Optionally, the endoscope assembly further comprises a special garment for colonoscopy patients to preserve the modesty of the patients and to protect a physician from spraying fecal matter.

20 Claims, 20 Drawing Sheets

Related U.S. Application Data

(60) Provisional application No. 62/162,078, filed on May 15, 2015, provisional application No. 62/117,362, filed on Feb. 17, 2015.

(51) Int. Cl.

| | | |
|---|---|---|
| *A61B 90/94* | (2016.01) | |
| *A61B 5/06* | (2006.01) | |
| *A61B 1/01* | (2006.01) | |
| *A61B 5/00* | (2006.01) | |
| *A61B 90/98* | (2016.01) | |
| *A61B 34/20* | (2016.01) | |

(52) U.S. Cl.
CPC ............ *A61B 5/0084* (2013.01); *A61B 90/94* (2016.02); *A61B 90/96* (2016.02); *A61B 90/98* (2016.02); *A61B 2034/2048* (2016.02); *A61B 2034/2065* (2016.02)

(58) Field of Classification Search
CPC .... A61B 2034/2046; A61B 2034/2048; A61B 2034/2055; A61B 2034/2057; A61B 2034/2065
See application file for complete search history.

(56) References Cited

U.S. PATENT DOCUMENTS

| | | |
|---|---|---|
| 4,027,697 A | 6/1977 | Bonney |
| 4,037,588 A | 7/1977 | Heckele |
| 4,402,313 A | 9/1983 | Yabe |
| 4,461,282 A | 7/1984 | Ouchi |
| 4,494,549 A | 1/1985 | Namba |
| 4,532,918 A | 8/1985 | Wheeler |
| 4,588,294 A | 5/1986 | Siegmund |
| 4,641,635 A | 2/1987 | Yabe |
| 4,764,001 A | 8/1988 | Yokota |
| 4,801,792 A | 1/1989 | Yamasita |
| 4,825,850 A | 5/1989 | Opie |
| 4,877,314 A | 10/1989 | Kanamori |
| 4,902,115 A | 2/1990 | Takahashi |
| 4,976,522 A | 12/1990 | Igarashi |
| 4,984,878 A | 1/1991 | Miyano |
| 5,007,406 A | 4/1991 | Takahashi |
| 5,014,685 A | 5/1991 | Takahashi |
| 5,193,525 A | 3/1993 | Silverstein |
| 5,224,929 A | 7/1993 | Remiszewski |
| 5,296,971 A | 3/1994 | Mori |
| 5,359,456 A | 10/1994 | Kikuchi |
| 5,395,329 A | 3/1995 | Fleischhacker |
| 5,447,148 A | 9/1995 | Oneda |
| 5,460,167 A | 10/1995 | Yabe |
| 5,464,007 A | 11/1995 | Krauter |
| 5,475,420 A | 12/1995 | Buchin |
| 5,489,256 A | 2/1996 | Adair |
| 5,518,501 A | 5/1996 | Oneda |
| 5,518,502 A | 5/1996 | Kaplan |
| 5,547,455 A | 8/1996 | McKenna |
| 5,547,457 A | 8/1996 | Tsuyuki |
| 5,575,755 A | 11/1996 | Krauter |
| 5,587,839 A | 12/1996 | Miyano |
| 5,630,782 A | 5/1997 | Adair |
| 5,630,798 A | 5/1997 | Beiser |
| 5,674,182 A | 10/1997 | Suzuki |
| 5,685,821 A | 11/1997 | Pike |
| 5,685,823 A | 11/1997 | Ito |
| 5,702,347 A | 12/1997 | Yabe |
| 5,725,474 A | 3/1998 | Yasui |
| 5,725,476 A | 3/1998 | Yasui |
| 5,725,477 A | 3/1998 | Yasui |
| 5,725,478 A | 3/1998 | Saad |
| 5,777,797 A | 7/1998 | Miyano |
| 5,782,751 A | 7/1998 | Matsuno |
| 5,800,341 A | 9/1998 | McKenna |
| 5,810,715 A | 9/1998 | Moriyama |
| 5,810,717 A | 9/1998 | Maeda |
| 5,810,770 A | 9/1998 | Chin |
| 5,830,121 A | 11/1998 | Enomoto |
| 5,870,234 A | 2/1999 | EbbesmeierneeSchitthof |
| 5,916,148 A | 6/1999 | Tsuyuki |
| 5,940,126 A | 8/1999 | Kimura |
| 6,058,109 A | 5/2000 | Lechleider |
| 6,095,970 A | 8/2000 | Hidaka |
| 6,095,971 A | 8/2000 | Takahashi |
| 6,181,481 B1 | 1/2001 | Yamamoto |
| 6,261,226 B1 | 7/2001 | McKenna |
| 6,277,064 B1 | 8/2001 | Yoon |
| 6,359,674 B1 | 3/2002 | Horiuchi |
| 6,402,738 B1 | 6/2002 | Ouchi |
| 6,419,626 B1 | 7/2002 | Yoon |
| 6,476,851 B1 | 11/2002 | Nakamura |
| 6,520,908 B1 | 2/2003 | Ikeda |
| 6,636,254 B1 | 10/2003 | Onishi |
| 6,638,214 B2 | 10/2003 | Akiba |
| 6,673,012 B2 | 1/2004 | Fujii |
| 6,690,337 B1 | 2/2004 | Mayer, III |
| 6,712,760 B2 | 3/2004 | Sano |
| 6,832,984 B2 | 12/2004 | Steizer |
| 6,888,119 B2 | 5/2005 | Iizuka |
| 6,997,871 B2 | 2/2006 | Sonnenschein |
| 7,154,378 B1 | 12/2006 | Ertas |
| 7,435,218 B2 | 10/2008 | Krattiger |
| 7,621,869 B2 | 11/2009 | Ratnakar |
| 7,630,148 B1 | 12/2009 | Yang |
| 7,701,650 B2 | 4/2010 | Lin |
| 7,713,246 B2 | 5/2010 | Shia |
| 7,746,572 B2 | 6/2010 | Asami |
| 7,813,047 B2 | 10/2010 | Wang |
| 7,828,725 B2 | 11/2010 | Maruyama |
| 7,918,788 B2 | 4/2011 | Lin |
| 7,927,272 B2 | 4/2011 | Bayer |
| 7,967,745 B2 | 6/2011 | Gilad |
| 7,976,462 B2 | 7/2011 | Wright |
| 8,064,666 B2 | 11/2011 | Bayer |
| 8,182,422 B2 | 5/2012 | Bayer |
| 8,197,399 B2 | 6/2012 | Bayer |
| 8,235,887 B2 | 8/2012 | Bayer |
| 8,287,446 B2 | 10/2012 | Bayer |
| 8,289,381 B2 | 10/2012 | Bayer |
| 8,300,325 B2 | 10/2012 | Katahira |
| 8,310,530 B2 | 11/2012 | Bayer |
| 8,353,860 B2 | 1/2013 | Boulais |
| 8,447,132 B1 | 5/2013 | Galil |
| 8,449,457 B2 | 5/2013 | Aizenfeld |
| 8,460,182 B2 | 6/2013 | Ouyang |
| 8,585,584 B2 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,797,392 B2 | 8/2014 | Bayer |
| 8,872,906 B2 | 10/2014 | Bayer |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,144,664 B2 | 9/2015 | Jacobsen |
| 9,289,110 B2 | 3/2016 | Woolford |
| 9,314,147 B2 | 4/2016 | Levy |
| 9,320,419 B2 | 4/2016 | Kirma |
| 9,867,669 B2 * | 1/2018 | Zhao ............... A61B 34/37 |
| 2001/0036322 A1 | 11/2001 | Bloomfield |
| 2002/0017515 A1 | 2/2002 | Obata |
| 2002/0087047 A1 | 7/2002 | Remijan |
| 2002/0109771 A1 | 8/2002 | Ledbetter |
| 2002/0109774 A1 | 8/2002 | Meron |
| 2002/0161279 A1 | 10/2002 | Luloh |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |

(56) References Cited

U.S. PATENT DOCUMENTS

| | | |
|---|---|---|
| 2003/0083552 A1 | 5/2003 | Remijan |
| 2003/0128893 A1 | 7/2003 | Castorina |
| 2003/0139650 A1 | 7/2003 | Homma |
| 2003/0153897 A1 | 8/2003 | Russo |
| 2003/0158503 A1 | 8/2003 | Matsumoto |
| 2003/0163029 A1 | 8/2003 | Sonnenschein |
| 2004/0015054 A1 | 1/2004 | Hino |
| 2004/0046865 A1 | 3/2004 | Ueno |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0057687 A1 | 3/2005 | Irani |
| 2005/0090709 A1 | 4/2005 | Okada |
| 2005/0096501 A1 | 5/2005 | Stelzer |
| 2005/0119527 A1 | 6/2005 | Banik |
| 2005/0124858 A1 | 6/2005 | Matsuzawa |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Bank |
| 2006/0063976 A1 | 3/2006 | Aizenfeld |
| 2006/0069314 A1 | 3/2006 | Farr |
| 2006/0111613 A1 | 5/2006 | Boutillette |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | DeLorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0270642 A1 | 11/2007 | Bayer |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036854 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0091065 A1 | 4/2008 | Oshima |
| 2008/0130108 A1 | 6/2008 | Bayer |
| 2008/0161646 A1 | 7/2008 | Gomez |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 9/2008 | Seibel et al. |
| 2008/0246771 A1 | 10/2008 | ONeal |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0168562 A1* | 7/2010 | Zhao ................... A61B 90/94 |
| | | 600/426 |
| 2010/0174144 A1 | 7/2010 | Hsu |
| 2010/0245653 A1 | 9/2010 | Bodor |
| 2010/0280322 A1 | 11/2010 | Mizuyoshi |
| 2010/0296178 A1 | 11/2010 | Genet |
| 2010/0326703 A1 | 12/2010 | Gilad |
| 2011/0004058 A1 | 1/2011 | Oneda |
| 2011/0004059 A1 | 1/2011 | Arneson |
| 2011/0063427 A1 | 3/2011 | Fengler |
| 2011/0084835 A1 | 4/2011 | Whitehouse |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211287 A1 | 9/2011 | Takata |
| 2011/0254937 A1 | 10/2011 | Yoshino |
| 2011/0263938 A1 | 10/2011 | Levy |
| 2011/0282144 A1 | 11/2011 | Gettman |
| 2011/0292258 A1 | 12/2011 | Adler |

(56) References Cited

U.S. PATENT DOCUMENTS

| | | |
|---|---|---|
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0162402 A1 | 6/2012 | Amano |
| 2012/0200683 A1 | 8/2012 | Oshima |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0281536 A1 | 11/2012 | Gell |
| 2012/0289858 A1 | 11/2012 | Ouyang |
| 2012/0300999 A1 | 11/2012 | Bayer |
| 2013/0053646 A1 | 2/2013 | Yamamoto |
| 2013/0057724 A1 | 3/2013 | Miyahara |
| 2013/0060086 A1 | 3/2013 | Talbert |
| 2013/0066297 A1 | 3/2013 | Shtul |
| 2013/0077257 A1 | 3/2013 | Tsai |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0253268 A1 | 9/2013 | Okada |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0184766 A1 | 7/2014 | Amling |
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | |
|---|---|---|
| CA | 2812097 | 3/2012 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 10540788 | 3/2016 |
| CN | 105377106 | 3/2016 |
| DE | 202010016900 | 5/2011 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | H1043129 | 2/1998 |
| JP | H10239740 | 9/1998 |

(56) References Cited

FOREIGN PATENT DOCUMENTS

| | | |
|---|---|---|
| JP | 11137512 | 5/1999 |
| JP | 2005253543 | 9/2005 |
| JP | 2006025888 | 2/2006 |
| JP | 2006068109 | 3/2006 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 | 12/2010 |
| WO | 2012038958 | 3/2012 |
| WO | 2012056453 | 5/2012 |
| WO | 2012077116 | 6/2012 |
| WO | 2012077117 | 6/2012 |
| WO | 2012096102 | 7/2012 |
| WO | 2012120507 | 9/2012 |
| WO | 2013014673 | 1/2013 |
| WO | 2013024476 | 2/2013 |
| WO | 2798716 | 6/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015112747 | 7/2015 |
| WO | 2015112899 | 7/2015 |
| WO | 2015095481 | 8/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

Office Action dated Jun. 28, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Action dated Jul. 22, 2016 for U.S. Appl. No. 14/549,265.
Sherman L.M., Plastics That Conduct Hear, Plastics Technology, Jun. 2001—article obtained online from http://www.ptonline.com/articles/plastics-that-conduct-heat.
Office Action dated Aug. 11, 2016 for U.S. Appl. No. 14/318,249.
Office Action dated Apr. 28, 2016 for U.S. Appl. No. 13/992,014.
Notice of Allowance dated Aug. 26, 2016 for U.S. Appl. No. 13/212,627.
Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.
Notice of Allowance dated Dec. 28, 2016 for U.S. Appl. No. 14/229,699.
Notice of Allowance dated Dec. 27, 2016 for U.S. Appl. No. 14/317,863.
Office Action dated Dec. 27, 2016 for U.S. Appl. No. 14/603,137.
Office Action dated Dec. 29, 2016 for U.S. Appl. No. 15/077,513.
Office Action dated Dec. 30, 2016 for U.S. Appl. No. 14/457,268.
Office Action dated Jan. 17, 2016 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,338.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action dated Mar. 20, 2017 for U.S. Appl. No. 14/278,293.
Notice of Allowance dated Mar. 21, 2017 for U.S. Appl. No. 14/549,265.
Office Action dated Mar. 22, 2017 for U.S. Appl. No. 14/705,355.
Office Action dated Mar. 24, 2017 for U.S. Appl. No. 14/838,509.
Notice of Allowance dated Apr. 12, 2017 for U.S. Appl. No. 14/603,137.
Notice of Allowance dated Apr. 18, 2017 for U.S. Appl. No. 13/713,449.
Office Action dated Apr. 19, 2017 for U.S. Appl. No. 14/988,551.
Notice of Allowability dated Apr. 21, 2017 for U.S. Appl. No. 14/549,265.
Office Action dated May 11, 2017 for U.S. Appl. No. 14/278,293.
Office Action dated May 10, 2017 for U.S. Appl. No. 14/988,551.
Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,986.
Office Action dated May 23, 2017 for U.S. Appl. No. 13/655,120.
International Search Report for PCT/US14/37004, dated Sep. 25, 2014.
International Search Report for PCT/US2014/037526, dated Oct. 16, 2014.
International Search Report for PCT/US14/38094, dated Nov. 6, 2014.
International Search Report for PCT/US2015/012751, dated Jun. 26, 2015.
International Search Report for PCT/US2014/58143, ated Jan. 21, 2015.

(56) References Cited

OTHER PUBLICATIONS

International Search Report for PCT/US2014/071085, dated Mar. 27, 2015.
International Search Report tor PCT/US2015/027902, dated Jul. 23, 2015.
International Search Report for PCT/US2015/012506, dated Dec. 11, 2015.
International Search Report for PCT/US2015/29421, dated Aug. 7, 2015.
International Search Report for PCT/US2015/28982, dated Jul. 28, 2015.
International Search Report for PCT/US2015/47334, dated Dec. 28, 2015.
International Search Report for PCT/US2015/41396, dated Sep. 29, 2015.
International Search Report for PCT/US2015/66466, dated Dec. 17, 2015.
International Search Report for PCT/US2015/6548, dated Feb. 26, 2016.
Office Action dated Feb. 26, 2016 for U.S. Appl. No. 14/274,323
Office Action dated Feb. 4, 2016 for U.S. Appl. No. 14/271,234.

\* cited by examiner

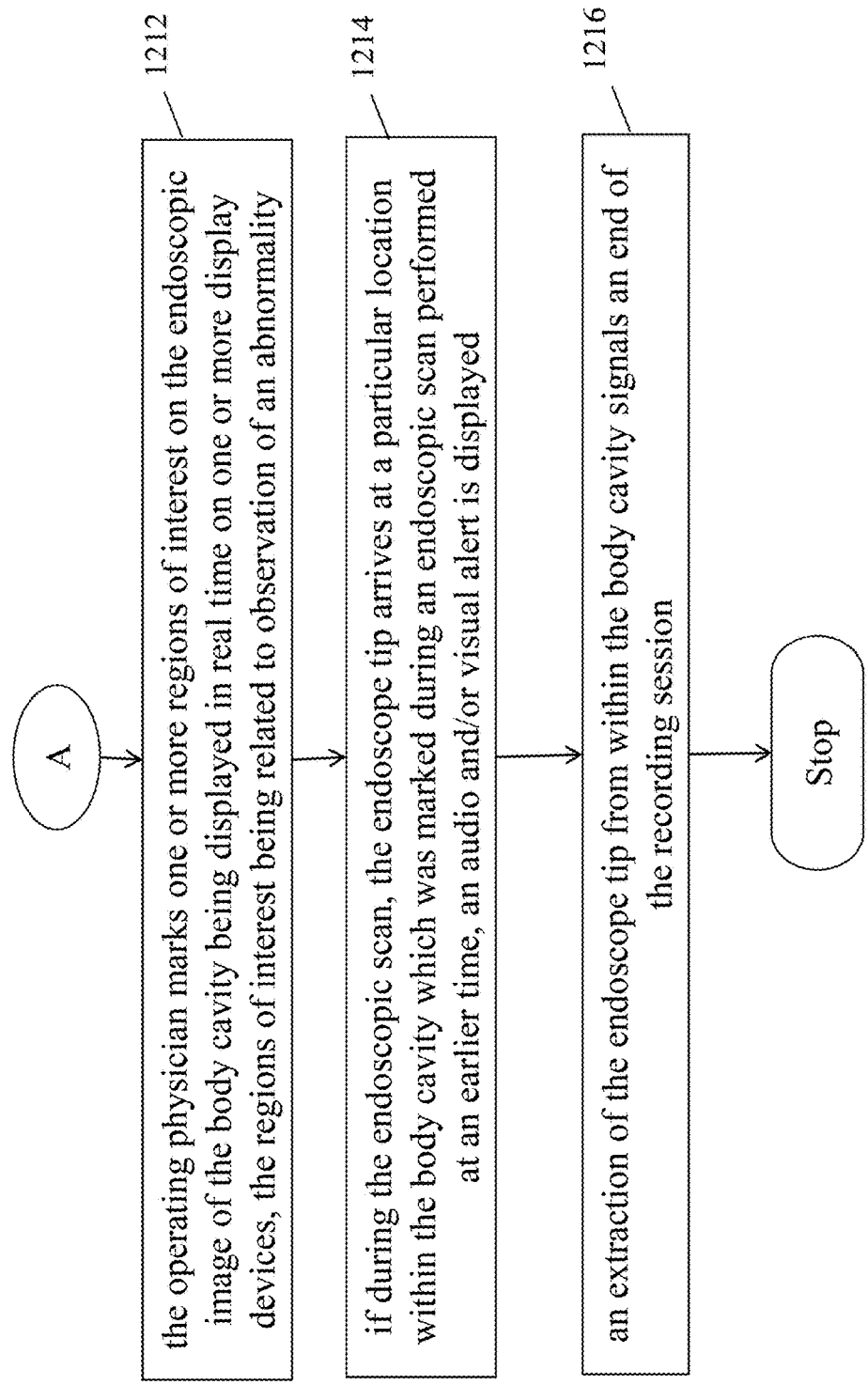
Figure 12 (contd.)

SYSTEM FOR DETECTING THE LOCATION OF AN ENDOSCOPIC DEVICE DURING A MEDICAL PROCEDURE

CROSS-REFERENCE

This application is a continuation of U.S. Nonprovisional patent application Ser. No. 15/045,590, filed on Feb. 17, 2016, which claims the benefit of priority of U.S. Provisional Patent Application No. 62/117,362, filed on Feb. 17, 2015, and U.S. Provisional Patent Application No. 62/162,078, filed on May 15, 2015.

The present application relates to U.S. patent application Ser. No. 13/655,120, entitled "Multi-Camera Endoscope" and filed on Oct. 18, 2012; U.S. patent application Ser. No. 13/212,627, entitled "Multi-Viewing Element Endoscope" and filed on Aug. 18, 2011; and U.S. patent application Ser. No. 13/190,968, entitled "Multi-Camera Endoscope" and filed on Jul. 26, 2011, all of which are continuation-in-part applications of U.S. patent application Ser. No. 13/119,032, entitled "Multi-Camera Endoscope" and filed on Jul. 15, 2011, which is a 371 National Stage Entry of PCT Application Number PCT/IL2010/000476, of the same title and filed on Jun. 16, 2010, which, in turn, relies upon U.S. Provisional Patent Application No. 61/218,085, for priority.

The present application also relates to U.S. patent application Ser. No. 14/505,387, entitled "Endoscope with Integrated Sensors", and filed on Oct. 2, 2014, and U.S. patent application Ser. No. 14/505,389, entitled "Endoscope with Integrated Sensors", and filed on Oct. 2, 2014, which, in turn, rely upon the following applications:

U.S. Provisional Patent Application No. 61/886,572, entitled "Endoscope with Integrated Location Determination", and filed on Oct. 3, 2013;

U.S. Provisional Patent Application No. 61/890,881, entitled "Endoscope with Integrated Pressure Sensing", and filed on Oct. 15, 2013; and U.S. Provisional Patent Application No. 61/980,682, entitled "System and Method for Monitoring the Position of a Bending Section of An Endoscope", and filed on Apr. 17, 2014.

The present application also relates to U.S. Provisional Patent Application No. 61/987,021, entitled "Real-Time Meta Tagging of Images Generated by A Multiple Viewing Element Endoscope", and filed on May 1, 2014.

The present application also relates to U.S. patent application Ser. No. 14/469,481, entitled "Circuit Board Assembly of A Multiple Viewing Elements Endoscope", filed on Aug. 26, 2014, which is herein incorporated by reference in its entirety along with all of the priority and related applications mentioned therein.

Each of the above-mentioned applications is herein incorporated by reference in its entirety.

FIELD

The present specification generally relates to systems for detecting the location of an endoscopic device inside a patient's body and in particular to a system for automatic tagging of images captured by endoscopic devices with such location information. In embodiments, the present specification also relates to a system and method for generating a real-time image map of the endoscopic device as it traverses a patient's lumen.

BACKGROUND

Medical probes such as endoscopes are used for examining and treating internal body structures such as the alimentary canals, airways, the gastrointestinal system, and other organ systems. Endoscopes have attained great acceptance within the medical community since they provide a means for performing procedures with minimal patient trauma while enabling the physician to view the internal anatomy of the patient. Over the years, numerous endoscopes have been developed and categorized according to specific applications, such as cystoscopy, colonoscopy, laparoscopy, upper gastrointestinal (GI) endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle, which sometimes includes an ocular lens or eyepiece for direct viewing. Viewing is also usually possible via an external screen. Various surgical tools may be inserted through a working channel in the endoscope for performing different surgical procedures.

Endoscopes typically have a front camera, and may also additionally include one or more side cameras, for viewing the internal organs, such as the colon, and an illuminator for illuminating the field of view of the camera(s). The camera(s) and illuminators are located in a tip of the endoscope and are used to capture images of the internal walls of the body cavity being scanned. The captured images are sent to a main control unit coupled with the endoscope via one of the channels present in the tube, for display on a screen coupled with the control unit.

In an endoscopy system, the main control unit, which is used to process data from an endoscope, is generally a separate unit while the endoscope itself is a device that can be attached to the main control unit. The main control unit comprises a front panel and/or a display screen for displaying operational information with respect to an endoscopy procedure when the endoscope is in use. The display screen may be configured to display images and/or video streams received from the viewing elements of the multiple viewing elements endoscope.

During an endoscopic procedure, it is important to record the location of findings or abnormalities noticed during the procedure. The location of any pathological structure, such as a polyp, inside the body can be defined by parameters such as insertion depth and the direction of the endoscope. None of the endoscopy systems currently available in the market provide a convenient method of estimating the insertion depth and direction of the device, with detailed position information, during a procedure. Position coordinates are generally provided by a physician based on a rough estimate, which are then manually input into the system to tag a specific image. In some conventional endoscopes, insertion tubes are marked with numbers which specify the depth of insertion at specified intervals from the tip section. The physicians are required to estimate the insertion depth from these numbers and manually input it into the system to tag images. However, this method is not accurate or convenient due to the wide spacing between marks and the need to manually input data.

Further, these endoscopy systems do not provide any means to accurately and/or automatically record the direction or rotational angle of an endoscope. There are endoscopy systems known in the art which use magnetic fields to estimate the location of the scope within the body; however, such devices are costly and cumbersome to use as they require external antennas to be set up for communication with the corresponding unit comprised in the distal tip of the scope. For example, ScopeGuide® by Olympus Corporation comprises electromagnetic coils emitting magnetic fields which are detected by antennae and triangulated to create a 3D image of the endoscope while inside a patient's body. In U.S. Pat. No. 6,610,007, Belson discloses an endoscope with "a selectively steerable distal portion and an automatically controlled proximal portion. The endoscope body is inserted into a patient and the selectively steerable distal portion is used to select a desired path within the patient's body. When the endoscope body is advanced, an electronic motion controller operates the automatically controlled proximal portion to assume the selected curve of the selectively steerable distal portion."

Conventional endoscopes also suffer from the drawback of having a limited field of view. The field of view is limited by the narrow internal geometry of organs as well as the insertion port, which may be one of the body's natural orifices or an incision in the skin. Further, in order to know the exact position/orientation of an endoscope tip within a body cavity, an operating physician has to usually rely on experience and intuition. The physician may sometimes become disoriented with respect to the location of the endoscope's tip, causing certain regions of the body cavity to be scanned more than once, and certain other regions to not be scanned at all. For the early detection and cure of many diseases, such as cancer, it is essential that the body cavity be examined in a manner such that no region remains un-scanned. Also, the precision of disease detection depends upon a thorough analysis of the images of the internal regions of the body cavity collected during multiple scans separated in time.

Further, with existing systems and methods, it is difficult and expensive to provide three dimensional imaging or video recording capabilities in an endoscopic device. To enable three dimensional imaging, a higher number of cameras and hardware, such as motion sensors, are required which significantly increases the size and cost of endoscopic devices. At the same time, there is an ever-increasing requirement to reduce the size of endoscopic devices to make the procedure convenient for patients. Therefore, it becomes difficult for equipment manufacturers to provide three dimensional imaging or real time video capabilities in the device.

Thus, what is needed is a method for measuring and recording location information (both depth and direction) during an endoscopic procedure to enable automatic tagging of images with this data. In addition, what is needed is a facile and inexpensive method to implement three-dimensional imaging capabilities in endoscopic devices. What is also needed is a method for providing real-time display of the device positioning within the body to enable better navigation capabilities.

What is also needed is a method for monitoring the complete movement of a device within the body and notifying physicians in case a deviation is detected from the normally expected movement. In addition, what is also needed is a method to monitor the speed, velocity and acceleration of the device inside the body.

There is also a need for a method enabling an operating physician to scan a body cavity efficiently ensuring complete and uniform coverage. Further, there is also a need for a system and method of connecting an endoscope with a plurality of devices at various geographically separated locations in order to enable sharing of endoscopic images in real-time for obtaining improved treatment options for a patient.

Many patients are not comfortable undergoing an endoscopic procedure, and in particular a colonoscopy, as private body parts are exposed to the medical staff during the procedure. Because of this reason, a large number of patients try to avoid colonoscopy examination for fear of embarrassment or violation of religious practices, leading to an increased risk of colon cancer in the population.

Thus, what is needed is an endoscopic system that can protect the privacy of patients during a procedure as it would lead to a significant number of people opting for a colonoscopy investigation who would have otherwise refrained from the same.

SUMMARY

The following embodiments and aspects thereof are described and illustrated in conjunction with systems, tools and methods, which are meant to be exemplary and illustrative, not limiting in scope.

The present specification discloses an endoscope assembly comprising: an endoscope comprising: an insertion tube having a length extending from a front panel of said endoscope to a handle of said endoscope and comprising on a surface throughout said length a plurality of codes indicative of insertion depth and direction of the endoscope when said insertion tube is inserted into a patient's body; a control handle coupled to said insertion tube and configured to control various functionalities of the endoscope; a detector configured to detect said plurality of codes and transmit data representative of said codes to a processor; and, a main control unit coupled to said control handle and comprising said processor, wherein said processor is adapted to estimate the insertion depth and direction of the endoscope based on said transmitted data.

Optionally, the processor estimates the insertion depth as the distance between said front panel of the endoscope and an external reference point. The external reference point may comprise the position of a patient's anus.

Optionally, the processor estimates the direction of the endoscope as angular rotation with respect to a predefined reference direction. The reference direction may extend in a perpendicular direction away from a patient's dorsal surface.

Optionally, each of said plurality of codes represents a unique set of values of insertion depth and rotational angle of the endoscope.

The plurality of codes may comprise at least one barcode or numbers representing the insertion depth at any position over the length of the insertion tube.

Optionally, the detector comprises a hollow cylindrical structure adapted to receive the insertion tube through the hollow portion of the detector and into the patient's body. The hollow cylindrical structure may comprise two hollow semi-circular cylindrical portions which are joined together to form the complete detector.

Optionally, the detector comprises a plurality of optical devices to capture the image of codes marked on the section of the insertion tube passing through the field of view of said optical devices. The optical devices may be embedded in the inner surface of a hollow cylindrical structure.

Optionally, images captured by said endoscopic device are tagged with a timestamp wherein the timestamp is used to associate an image with an insertion depth and direction of an endoscope.

Optionally, the endoscope further comprises a tip section adapted to capture images and said processor is further adapted to receive data representative of said images, wherein data of multiple images captured by said tip section is merged with insertion depth and direction information to generate three dimensional images or videos.

Optionally, the endoscope assembly further comprises a garment to be worn by the patient for colonoscopy procedures and configured such that a rear section of the garment is re-positionable to expose an opening for performing a colonoscopy procedure wherein said garment is configured to provide support for attaching and securing the detector. The rear section may comprise at least one of covers, flaps, Velcro straps, buckles, and zippers configured to re-position the rear section and expose said opening. The garment may comprise underwear.

Optionally, the processor is further adapted to calculate the acceleration and speed of a distal tip of the endoscope inside the patient's body based on the incremental change in values of insertion depth and direction of the endoscope. The processor may be adapted to compare the acceleration or speed of said distal tip with predefined standard parameters to detect inadequate screening due to incomplete rotation or fast movement of the endoscope. The processor may be further adapted to activate an alert to notify the physician when inadequate screening is detected.

Optionally, the detector comprises a hollow truncated conical structure adapted to receive the insertion tube through the hollow portion of the detector and into the patient's body.

Optionally, the detector comprises a ring shaped base unit and at least one vertical structure coupled to said base unit wherein said vertical structure comprises a plurality of optical devices.

Optionally, the endoscope assembly is used to estimate the actual size of a pathological structure in the body by combining two separate images of said pathological structure captured from two insertions whose depth difference is known.

The present specification also discloses a garment designed for a patient having a colonoscopy procedure comprising a rear section which is re-positionable to expose an opening for performing the colonoscopy procedure while simultaneously protecting the modesty of the patient by preventing complete exposure of the patient's private body parts. The garment may comprise underwear. The garment may be configured to provide support for firmly attaching a detector to the garment wherein said detector is configured to detect markings along the length of an outer surface of an insertion tube of the colonoscope, further wherein said markings are indicative of insertion depth and direction of the colonoscope.

The present specification also discloses an endoscope comprising at least a first sensor on a distal end of a tip portion for capturing and transmitting location information of the distal tip within a lumen during an endoscopic procedure, the location information being processed to obtain a real time endoscopic image map of the tip portion traversing the lumen.

Optionally, the endoscope further comprises a second sensor provided at a location outside the lumen for receiving the location information of the distal tip within the lumen during the endoscopic procedure.

The endoscopic image map may be displayed on one or more display devices coupled with the endoscope for providing a real time location of the endoscope tip within the lumen.

Optionally, the first sensor transmits the location information of the distal tip within the lumen by using wireless signals in the sub-gigahertz frequency field.

The first and second sensors may be any one of an accelerometer, a gyro sensor, and a radar based sensor.

The second sensor may be placed at a pre-defined location on the body of a patient undergoing the endoscopic procedure, the location being in close proximity to the point of insertion of the endoscope into the lumen, or may be placed at a pre-defined location on the bed of the patient undergoing the endoscopic procedure.

Optionally, the second sensor provides a reference plane for obtaining a real time position of the distal end of the tip of the endoscope and a pre-defined algorithm is used to process the reference plane and the location information to provide the real time endoscopic image map of the tip portion traversing the lumen.

The present specification also discloses a method of obtaining a real time image map of an endoscope tip scanning a lumen during an endoscopic procedure, the method comprising the steps of: recording an initial position of the endoscope tip within the lumen as zero coordinates; obtaining a current position of the endoscope tip within the lumen; constructing a real time image map of the endoscope tip scanning the lumen by mapping the current position of the tip with reference to the zero coordinates; and displaying the image map on one or more display devices in real time.

Optionally, the method further comprises the step of storing the real time images in a database, the stored images being used to perform analytical operations using images obtained from one or more previously conducted endoscopic procedures and a pre-defined algorithm.

Optionally, the method further comprises the step of marking one or more regions of interest on the displayed images, the regions of interest being related to observation of an abnormality, the marking comprising a comment describing the abnormality.

Optionally, the method further comprises the steps of commencing a recording session when the endoscope tip is inserted into the lumen and stopping the recording session when the endoscope tip is extracted from the lumen.

The present specification also discloses an endoscope comprising: a tip having a distal end and a proximal end, the distal end being inserted into a body cavity during an endoscopic procedure, and a navigation sensor coupled with the distal tip for capturing and transmitting a location information of the distal tip within the body cavity; a handle portion coupled with the proximal end of the tip; and a main control unit receiving the location information of the distal tip within the body cavity, the main control unit being coupled with the handle portion, the main control unit comprising a wireless module connecting the main control unit to the Internet for transmitting the location information to one or more devices.

Optionally, a second sensor is coupled with the handle portion for receiving the location information and transmitting the same to the main control unit.

The wireless module may establish a link over one or more secured Internet standards for transmitting live video of endoscopic procedures from the main control unit to one or more display devices. The wireless module may be used for transmitting live video of endoscopic procedures from the main control unit to one or more cellular phones present within a pre-defined range, the cellular phones having a pre-defined application installed therein, the cellular phones being used for broadcasting the endoscopic procedures and comparing a current endoscopic procedure with one or more previously conducted procedures stored in a database via the installed application.

The present specification also discloses an endoscope comprising: a first sensor on a distal end of a tip portion of the endoscope for capturing and transmitting location information of the distal tip within a lumen during; and a second sensor in communication with the first sensor, the second sensor provided at a location outside the lumen for receiving the location information during an endoscopic procedure.

Optionally, the endoscope further comprises at least one wireless module in communication with at least one of the first sensor and the second sensor for wirelessly transmitting location information.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein.

DETAILED DESCRIPTION

Figure 1A:
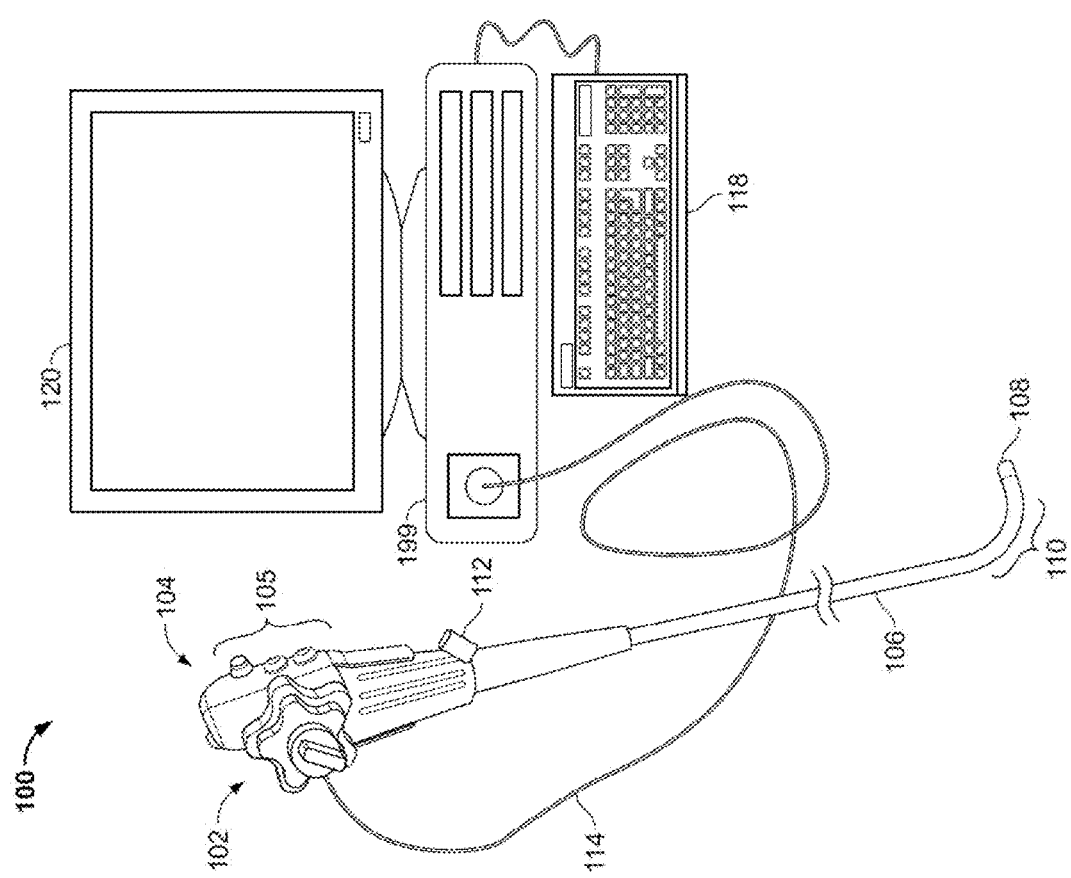
FIG. 1A illustrates a multiple viewing element endoscopy system in accordance with an embodiment of the present specification.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It is noted that the term "endoscope" as mentioned to herein may refer particularly to a colonoscope or gastroscope, according to some embodiments, but is not limited only to colonoscopes or gastroscopes. The term "endoscope" may refer to any instrument used to examine the interior of a hollow organ or cavity of the body.

The capability for recording the exact depth and direction of an endoscopic device inside a human body is imperative for tagging the location of any pathological structure, such as a polyp or any other kind of abnormality, inside the body. Conventional endoscopy systems do not automatically record the location or insertion depth of the endoscopic device inside a patient's body. In some conventional endoscopes, insertion tubes are marked with numbers which specify the depth of insertion at specified intervals from the tip section.

In addition, current endoscopy systems do not provide any means to record the direction or rotational angle of an endoscope. Also, current endoscopy systems are not equipped to monitor the acceleration of the device inside the body and hence cannot detect and indicate occurrences when there is inadequate screening due to incomplete rotation or fast movement of the device.

The present specification describes an endoscopy system having the capability to automatically detect the location of a device inside a patient's body and tag images captured by the viewing elements of the endoscopic device with this information. In an embodiment, the insertion depth and rotational angle of the section of the endoscopic device present inside the body are recorded in real time. In an embodiment, the insertion tube of the endoscopic device is marked with a set of codes that aid in establishing the insertion depth of the device with respect to a reference point and the rotational angle of the device with respect to a reference direction. The endoscopy system also comprises a detector or a reading device to detect/read these codes from the insertion tube as the device is lowered into a patient's lumen to establish the depth and direction of the endoscope with respect to reference parameters, such as a reference point or a reference direction. In an embodiment, a reference point for measuring the insertion depth of an endoscope is a front panel of the tip section of the endoscope. In an embodiment, a reference direction for measuring the direction of an endoscope is a vector pointing in the direction of the tailbone of the patient. In some embodiments, the detector comprises cameras or optical readers to read the codes marked on the insertion tube.

In an embodiment, the present specification provides a method of obtaining real time position of an endoscope tip within a body cavity during an endoscopic scan procedure. Embodiments of the present specification enable an operating physician to view a current position of the endoscope tip within the lumen being scanned, on a display device coupled with the endoscope.

One of ordinary skill in the art would appreciate that there may be multiple ways to develop the coding system for marking the insertion tube to ascertain the location of an endoscopic device without departing from the scope and spirit of the present specification. In an embodiment, an insertion tube is marked with barcodes along its length and circumference wherein each barcode comprises a unique set of values indicative of the insertion depth and rotation angle corresponding to the area marked by said barcode. In this embodiment, the detector or reading unit comprises a barcode reader. One of ordinary skill in the art would appreciate that various types of barcodes could be used in the above embodiment. A barcode is an optical machine-readable representation of data relating to the object to which it is attached. In various embodiments, liner barcodes comprising various combinations of parallel lines and/or two dimensional barcodes, which comprise geometric patterns such as rectangles and dots, are marked on an insertion tube for readying by a detector.

In some embodiments of the present specification, instead of the codes marked over the outer surface of the endoscopic device, a plurality of passive RF-ID (Radio Frequency Integrated Devices) are positioned under the outer layers of the endoscope insertion tube. In this case each RFID corresponds to a unique set of values of the insertion depth and rotational angle of the endoscopic device in the patient body. A detector/reading unit in the form of a RF reader is used to scan the RFIDs distributed under the outer layer of the endoscope to detect the location information of an endoscopic device as it is inserted into a body lumen.

In an embodiment, the detector/reading unit is a discrete unit from the rest of the endoscopy system and is coupled to the patient's body to detect the codes marked on the insertion tube and establish the insertion depth and rotation angle of the endoscope. One of ordinary skill in the art would appreciate that there may be multiple ways to position the detection device. In an embodiment, for example, in a colonoscopy procedure, the detector/reading unit is attached or fixed to a garment worn by the patient. In another embodiment, the detector/reading unit is positioned in a special holder or housing to read the corresponding codes on the insertion tube. In an embodiment, the holder or housing containing the detector/reading unit is firmly coupled or attached to the patient. In another example, in a gastroscopy procedure, the detector/reading device is attached to a specially designed mouth piece. In an embodiment, mouth pieces commonly used in gastroscopy procedures are configured to incorporate features such that a reading/detector unit can be firmly coupled to the mouth piece.

In an embodiment, for colonoscopy procedures, the present specification discloses a garment, wearable by a patient and configured to securely hold a detector/reading unit, wherein the detector/reading unit detects/reads codes provided on an insertion tube of an endoscope as the endoscope is inserted into the anus of the patient. In an embodiment, the patient garment comprises underwear to which a detector/reading unit, such as an optical reader, is attached.

The use of a specific garment to hold the detector/reading unit provides an added benefit of maintaining the modesty/privacy of patients undergoing a colonoscopy procedure. A large number of patients try to avoid colonoscopy investigation for fear of embarrassment or violation of religious practices as they have to expose their private body parts to the medical staff. In an embodiment, the patient garment described in the present specification prevents the complete exposure of the patient's private body parts, thereby maintaining his or her modesty to a certain extent.

In the above mentioned embodiments, a detector/reading unit and an endoscopic device are initially aligned to a specific reference point and a reference direction. All changes in the position of the endoscopic device are measured relative to these reference parameters to establish any incremental change in depth or direction.

In an embodiment, the system described in the present specification provides an inexpensive and efficient method of creating three-dimensional (3D) still images or live videos without increasing the size of a distal tip of an endoscope. Usually, a higher number of cameras and motion sensors is required to create 3D images or video which significantly increases the size and cost of endoscope devices. The present specification provides an inexpensive method of creating 3D still images or live videos by fusing or merging 2D image data recorded at varying levels of depth and rotational angles.

In an embodiment, the present specification also provides a method for estimating the size and location of pathological structures, such as polyps.

In an embodiment, the present specification enables easier navigation for physicians who are not adept in navigating an endoscopic device without additional information on the depth and rotational angle. In an embodiment, the present specification provides means for displaying the insertion depth and rotational angle of an endoscope along with an image of the distal tip inside a patient's lumen in real time.

In another embodiment, with the aid of depth and direction data, a system processor monitors the acceleration of an endoscopic device inside a patient's body and issues automatic alerts, notifications or warnings. The speed at which the endoscopic device is moving through the patient's body is measured by calculating the difference, both in insertion depth and in timing of detection, between two consecutive readings of markings on the endoscopic device by the processor. Specifically, a processor receives data indicative of a time stamped insertion depth from an optical reading device. Periodically, the processor calculates a speed of insertion by determining a first insertion depth and its first associated time, determining a second insertion depth and its second associated time, obtaining a difference between the second insertion depth and first insertion depth, obtaining a difference between the first associated time and second associated time, and dividing the two differences.

In an embodiment, notifications are issued if an endoscopic device is pushed or pulled too fast for reliable detection of pathological structures or for safe traverse of a body lumen. Specifically, a threshold speed value is stored in a memory and compared, on a real-time basis, to the speed determined as described above. When the calculated speed exceeds the threshold speed, as determined by the processor, the processor issues a notification in the form of a signal to a vibrator in the endoscope handle, a signal to an audio speaker in the display, or a signal to the display to visually present an icon, image, color, or other picture. In another embodiment, automatic notifications are issued if a device is not rotated fully to cover an entire 360 degrees with the side cameras of an endoscope. In embodiments of the present specification, the optimal speed of the movement of a tip section for scanning a specific section of a lumen is predetermined and input into the endoscopic system. In an alternate embodiment, the endoscopic system is intelligent and determines the optimal speed for scanning various sections of the lumen based on historical data. In an embodiment, the historical data comprises the scanning speed used for scanning a section of lumen during various procedures conducted in the past. In case there is significant deviation from these optimal reference speeds, appropriate notifications are issued to the physician.

In an embodiment, the present specification discloses a novel endoscopy system comprising a plurality of sensors for generating a real time image map of the endoscopic tip portion traversing a body lumen. In an embodiment, a first sensor device is deployed on the tip section of the endoscope for capturing and transmitting location information of the distal tip within a lumen and a second sensor device is deployed at a location outside the lumen for receiving the location information of the distal tip within the lumen during a procedure. Embodiments of systems and methods enable mapping images captured by the endoscope from within the lumen in real time and placing the captured images in a reference frame. A method of the present specification enables an operating physician to perform a complete endoscopic scan of a body cavity during a single scanning session, without missing any region therein. Embodiments of the specification also provide a method of transmitting data from within a body lumen in real time, thereby providing an accurate location of an endoscope tip within the lumen on a display device coupled with the endoscope. The coordinates of the endoscope tip within the lumen are recorded in real time, thereby providing a map of the areas of the lumen scanned by the endoscope. Embodiments of the specification also provide a method of marking regions of interest within the captured images mapped onto the pre-defined reference frame and recording one or more of the physician's findings corresponding to the marked regions. The markings enable comparisons between the marked regions across images captured at different times/dates. Thus, various embodiments of the specification enable early detection of diseases.

The present specification also provides a method of wirelessly transmitting endoscope scan data from a main control unit of the endoscope to one or more devices, including mobile devices and display devices. The present specification also provides a method for live streaming of an endoscopic scanning procedure of a body cavity on multiple devices, such as mobile devices and display devices.

Reference is now made to FIG. 1A, which shows a multiple viewing elements endoscopy system 100 in which the insertion depth and direction detection system, as well as the real time image mapping method, of the present specification can be implemented. In an embodiment, the system 100 includes a multiple viewing elements endoscope 102. In an embodiment, the multiple viewing elements endoscope 102 includes a handle 104, from which an elongated shaft 106 emerges. Elongated shaft 106 terminates with a tip section 108 which is turnable by way of a bending section 110. Handle 104 is used for maneuvering elongated shaft 106 within a body cavity. The handle 104 includes one or more buttons and/or knobs and/or switches 105 which control bending section 110 as well as functions such as fluid injection and suction. Handle 104 further includes at least one working channel opening 112 through which surgical tools may be inserted.

A utility cable 114, also referred to as an umbilical tube, connects between handle 104 and a main control unit 199. Utility cable 114 includes therein one or more fluid channels and one or more electrical channels. The electrical channel(s) includes at least one data cable for receiving video signals from front and side-pointing viewing elements of the endoscope 102, as well as at least one power cable for providing electrical power to the viewing elements and to discrete illuminators.

The main control unit 199 contains the controls required for displaying the images of internal organs captured by the endoscope 102. In an embodiment, the main control unit 199 governs power transmission to the endoscope's 102 tip section 108, such as for the tip section's viewing elements and illuminators. In an embodiment, the main control unit 199 further controls one or more fluid, liquid and/or suction pump(s) which supply corresponding functionalities to the endoscope 102. In embodiments, one or more input devices 118, such as a keyboard, a touch screen and the like are connected to the main control unit 199 for the purpose of human interaction with the main control unit 199. In the embodiment shown in FIG. 1A, the main control unit 199 is connected to a screen/display 120 for displaying operation information concerning an endoscopy procedure when the endoscope 102 is in use. The screen 120 is configured to display images and/or video streams received from the viewing elements of the multiple viewing elements endoscope 102. The screen 120 may further be operative to display a user interface for allowing a human operator to set various features of the endoscopy system 100.

Optionally, the video streams received from the different viewing elements of the multiple viewing elements endoscope 102 are displayed separately on at least one monitor/screen 120 by uploading information from the main control unit 199, either side-by-side or interchangeably (namely, the operator may switch between views from the different viewing elements manually). Alternatively, these video streams are processed by the main control unit 199 to combine them into a single, panoramic video frame, based on an overlap between fields of view of the viewing elements. In an embodiment, two or more displays are connected to the main control unit 199, each for displaying a video stream from a different viewing element of the multiple viewing elements endoscope 102.

Figure 1B:
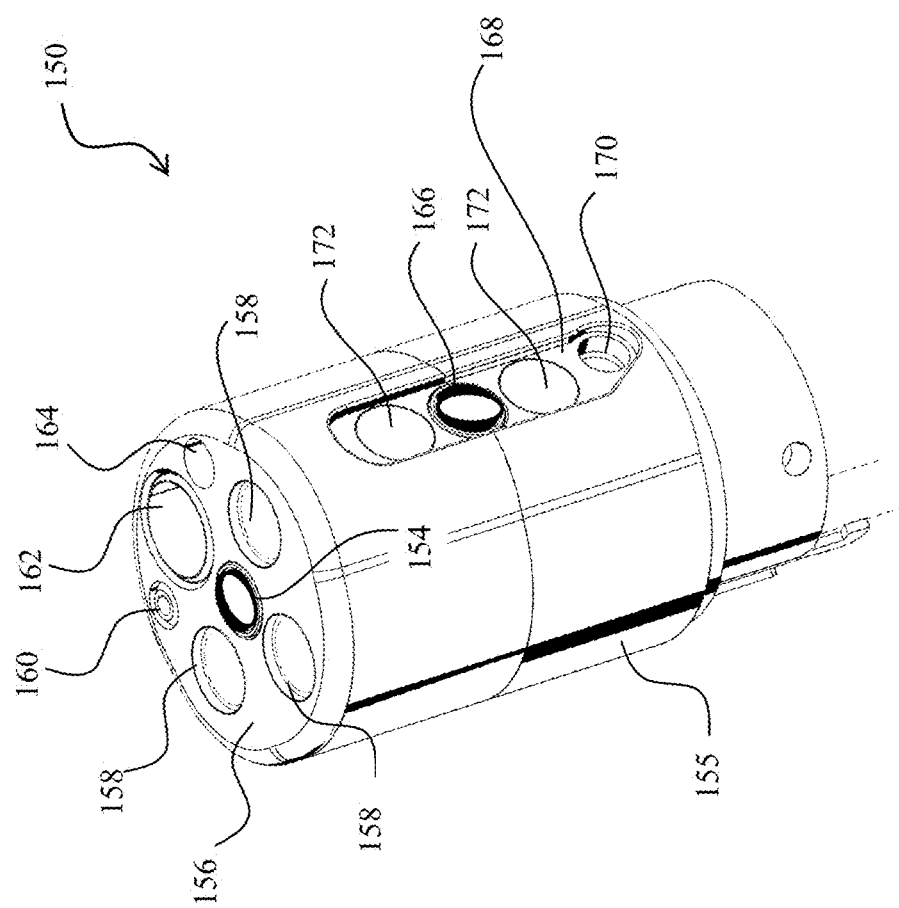
FIG. 1B illustrates a perspective view of a tip section of a multiple viewing element endoscope in accordance with an embodiment of the present specification.

Referring to FIG. 1B, a perspective view of a tip section 150 of a multiple viewing elements endoscope is shown. In an embodiment, the tip section 150 includes therein a front-pointing viewing element 154 which captures images through a hole in a distal surface 156 of tip section 150.

At least one discrete front illuminator 158, which is, in an embodiment, a light-emitting diode (LED), is associated with front-pointing viewing element 154 and is used for illuminating its field of view through another hole in distal end surface 156. In embodiments of the present specification, the LED comprises a white light LED or an infrared light LED or a near infrared light LED or an ultraviolet light LED, or a combination of wavelengths. The term "discrete", in regard to front illuminator 158, may refer to an illumination source which generates light internally—in contrast to a non-discrete illuminator which may be, for example, a fiber optic merely transmitting light generated remotely. In another embodiment, two or more discrete front illuminators 158 are present on distal surface 156 of tip section 150, for supplying overall stronger illumination and/or for increasing the angular coverage of the illumination. In an embodiment, these two or more discrete front illuminators are located next to one another so that they share a same protective window on distal surface 156.

A front fluid injector 160 is used for cleaning at least one of front-pointing viewing element 154 and discrete front illuminator 158. In an embodiment, the distal end surface 156 includes a hole defining a working channel 162, which may be a hollow tube configured for insertion of a surgical tool to operate on various tissues. A pathway fluid injector 164, defined by another hole in distal end surface 156, is used for inflating and/or cleaning the body cavity into which endoscope tip 150 is inserted.

In an embodiment, the tip section 150 further includes therein a side-pointing viewing element 166 which captures images through a hole in a cylindrical surface 155 of the tip section. At least one discrete side illuminator 172, which is optionally similar to discrete front illuminator 158, is associated with side-pointing viewing element 166 and used for illuminating its field of view through another hole in cylindrical surface 155. In an embodiment, a side fluid injector 170 is used for cleaning at least one of side-pointing viewing element 166 and discrete side illuminator 172.

In another embodiment, two or more discrete side illuminators 172 are present in the tip section 150, such as for supplying overall stronger illumination and/or for increasing the angular coverage of the illumination. In an embodiment, these two or more discrete side illuminators are located next to one another so that they share a same protective window on the cylindrical surface of the tip section. In order to prevent tissue damage when cylindrical surface 155 of tip section 150 contacts a side wall of the body cavity, side fluid injector 170, side-pointing viewing element 166, and side illuminators 172 are optionally located in a notch or depression 168 in cylindrical surface 155. In this manner, side fluid injector 170 is elevated from depression 168 but still may not significantly protrude from the level of cylindrical surface 155. The elevation of side fluid injector 170 enables it to inject fluid onto side-viewing element 166 and discrete side illuminators 172. In yet another embodiment, a side-viewing element, one or more side illuminators and a side fluid injector are not located in a depression, but are at the same level as cylindrical surface of the tip section. In various embodiments, another side-viewing element, one or more side illuminators, and another side fluid injector are positioned on an opposite side of surface 155 from side-viewing element 166, side illuminators 172, and side fluid injector 170 to provide an additional field of view.

Endoscopic Position Determination

Figure 2A:
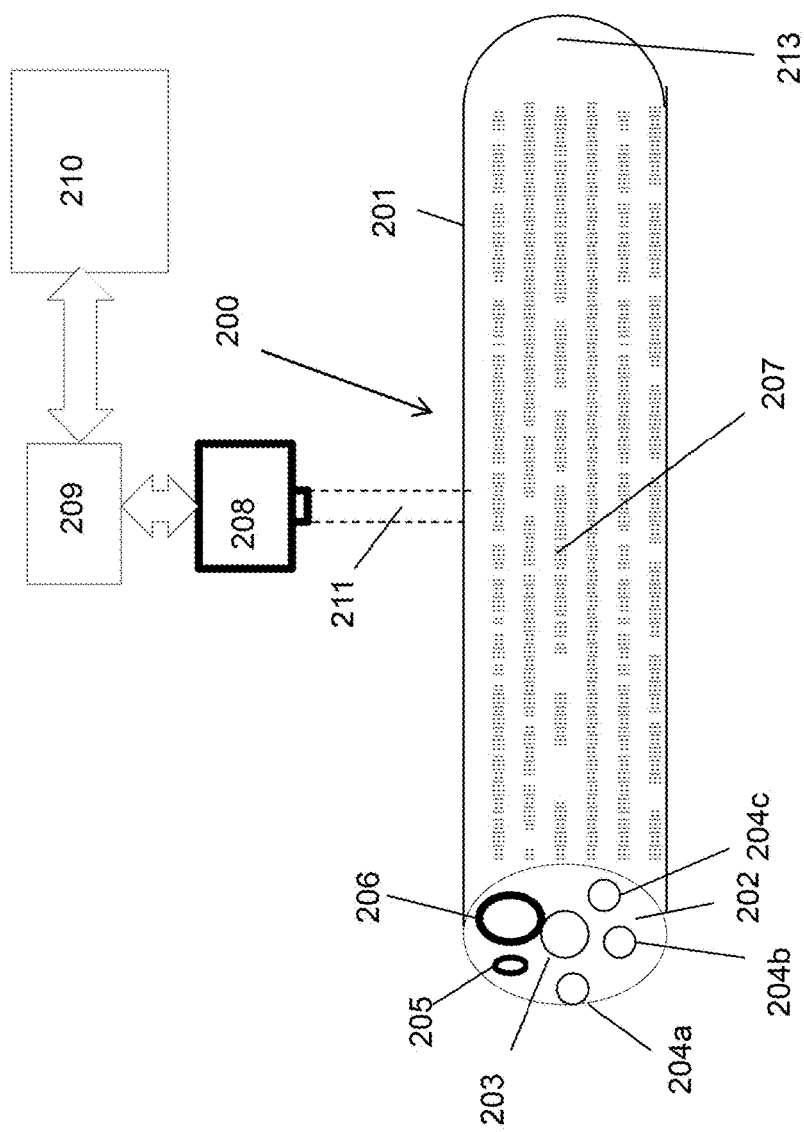
FIG. 2A illustrates a portion of an insertion tube of an endoscopic device in accordance with an embodiment of the present specification.

FIG. 2A illustrates a portion of an insertion tube 200 of an endoscopic device in accordance with an embodiment of the present specification. As shown in FIG. 2A, the insertion tube 200 comprises a distal section 201 which includes a front panel 202 at its distal end. The front panel 202 comprises a front viewing element 203. Front illuminators 204a, 204b and 204c illuminate the field of view of viewing element 203. A front working channel opening 206 allows the physicians to insert medical tools into and through a working channel of the endoscope and perform procedures on target areas viewed through the front viewing element 203. In another embodiment, a jet channel opening 205 of a jet channel is located on front panel 202. Jet channel opening 205 is configured to provide high-pressure jets of fluid, such as water or saline, for cleaning the walls of a body cavity being viewed.

In an embodiment, the insertion tube 200 comprises a plurality of codes 207 marked over its external surface or cover. The insertion tube 200 is an elongate, tubular section of the endoscopic device having a length, a proximal end and a distal end and configured to be inserted into a lumen of a patient. In some embodiments, the proximal end 213 of the insertion tube is defined by a distal end of the endoscope handle (104 in FIG. 1A) and the distal end of the insertion tube is defined by the front panel 202. In some embodiments, the plurality of codes 207 extends along the entire length and about the entire circumference of the insertion tube 200, extending from the handle to the front panel 202. In other embodiments, the plurality of codes 207 extends along only a portion of the length of the insertion tube 200. In some embodiments, each code within the plurality of codes 207 corresponds to a unique set of longitudinal and rotational data relative to certain predefined reference parameters. In an embodiment, this data is indicative of the location information of a specific point or area on the insertion tube 200 associated with the position of the code on the tube 200. The detector/reading unit 208 is configured to detect/read the codes marked on the section of insertion tube 200 that passes through its field of view 211 as the endoscopic device is inserted into the patient's body. In an embodiment, the reading unit 208 is in data communication with a processor 209 which is configured to receive the information on codes 207 detected by detector/reading unit 208, decrypt this information to estimate the insertion depth and rotational angle and, in an embodiment, transmit the decrypted information further to the main control unit 210 of the endoscope assembly. In some embodiments, the detector/reading unit 208 and processor 209 are a unified unit. In other words, in some embodiments, the processor 209 is housed within the detector/reading unit 208. In some embodiments, the processor 209 performs minimal processing and is mainly responsible for transferring raw readings to the main control unit 210. In other embodiments, the processor 209 is responsible for complete depth, rotation, speed, and acceleration analysis and passes the resulting data to the main control unit 210. In still other embodiments, the processor 209 is also responsible for sending video obtained by scanning cameras to the main control unit 210.

One of ordinary skill in the art can appreciate that there may be multiple ways to develop the coding scheme and to define the reference parameters. In some embodiments, the reference points for measuring the longitudinal information or the insertion depth are the front panel 202 and the detector/reading unit 208, wherein the distance between the front panel 202 and the detector/reading unit 208 signifies the insertion depth of the endoscopic device at any given position. In this embodiment, each code within the plurality of codes 207 is indicative of a relative distance from the front panel 202. The codes marked along the circumference of the insertion tube 207 at a specific depth indicate the same distance from the front panel 202.

In some other embodiments, the reference points for measuring the longitudinal information or the insertion depth are the front panel 202 and the position of a patient's anus, wherein the distance between the front panel 202 and anus signifies the insertion depth of the endoscopic device at any given position. In this embodiment, the coding scheme is devised such that each of the codes 207 indicate the distance between the front panel 202 and the patient's anus which provides an estimate of the depth at which investigation is performed.

In some embodiments, the angular movement or rotation of the endoscopic device inside the body is measured with respect to the direction of some external reference point, such as a patient's tailbone. In various embodiments of the present specification, angular movement of the endoscopic device is defined as the angle of rotation of the entire insertion tube along its longitudinal axis. Angular movement occurs as the physician turns his palm while manipulating the endoscopic device, causing the insertion tube to rotate about the longitudinal axis of the device.

Figure 3A:
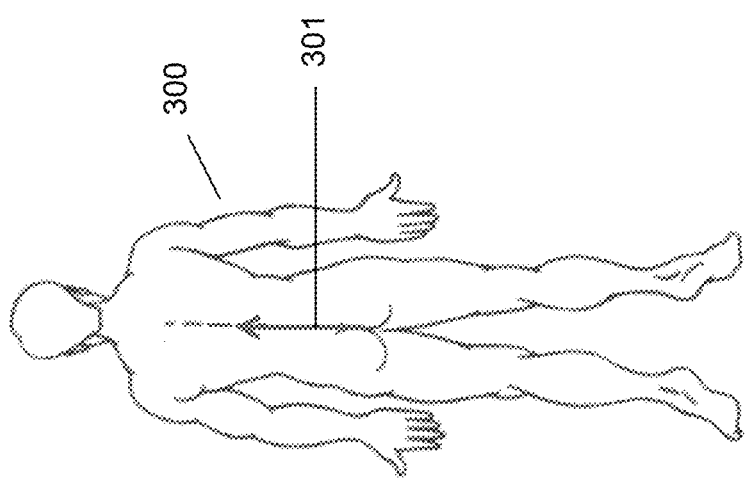
FIG. 3A depicts a vertical arrow in the direction of a patient's tailbone, showing an external reference point.
Figure 3B:
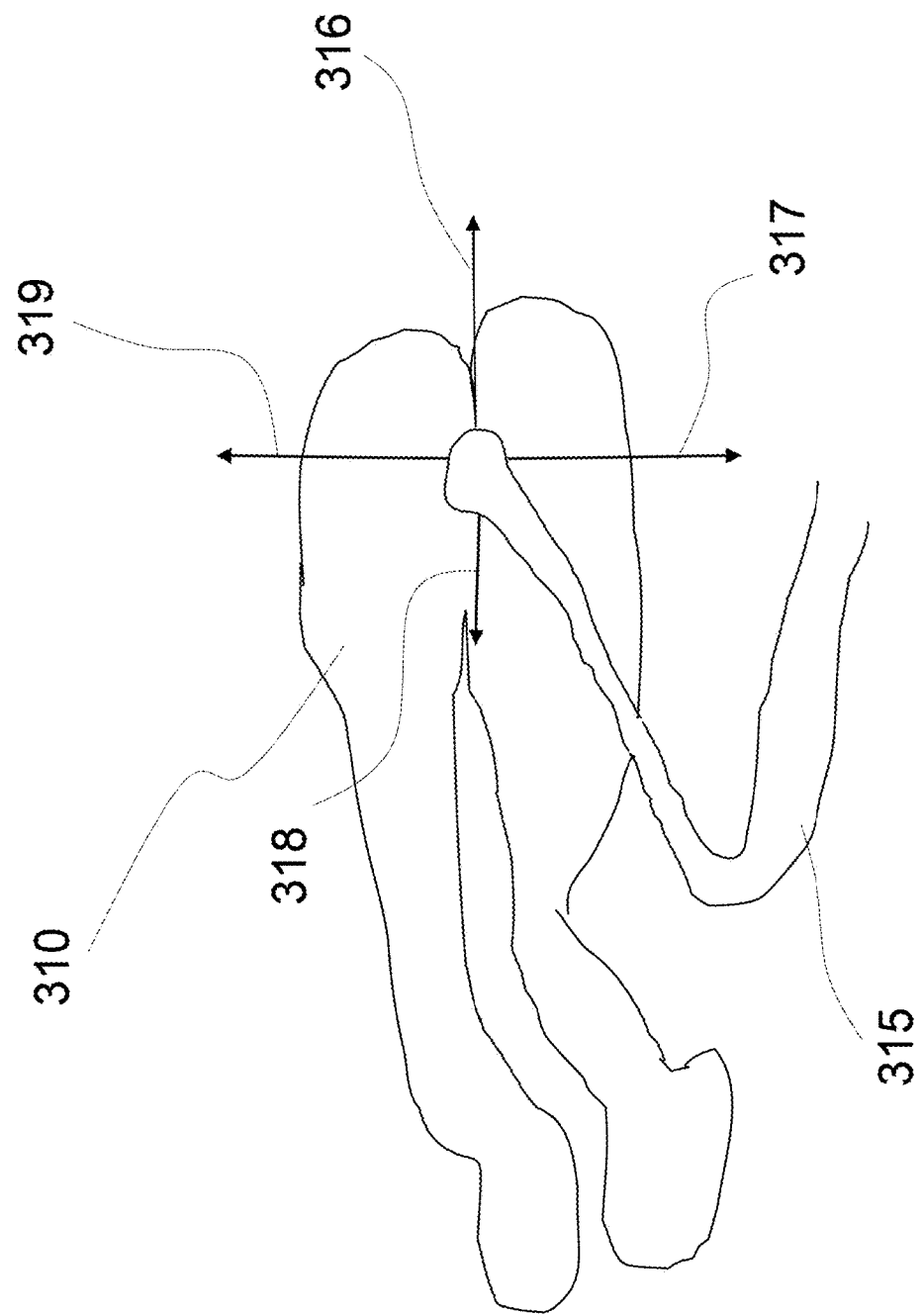
FIG. 3B is an illustration of a patient lying on his right side with an insertion tube of an endoscopic device inserted into the patient's anus.

Reference is made to FIG. 3A, which shows a person 300 with arrow 301 extending in a cephalic direction (toward the person's head) along a dorsal surface of the person with respect to the person's tailbone. Arrow 301 indicates the insertion direction of an endoscopic device as the insertion tube is introduced into a patient's anus. FIG. 3B is an illustration of a patient 310 lying on his right side with an insertion tube 315 of an endoscopic device inserted into the patient's 310 anus. Arrow 316 illustrates a direction extending perpendicularly away from a dorsal surface of the patient 310 and, in various embodiments, indicates a 0° reference angle for angular movement of the insertion tube 315. Arrow 317 illustrates a direction extending perpendicularly away from a right side of the patient 310 and, in various embodiments, indicates a 90° rotational angle in a clockwise direction, or 270° rotational angle in a counter-clockwise direction, for angular movement of the insertion tube 315 with respect to the 0° reference angle indicated by arrow 316. Arrow 318 illustrates a direction extending perpendicularly away from a ventral surface of the patient 310 and, in various embodiments, indicates a 180° rotational angle for angular movement of the insertion tube 315 with respect to the 0° reference angle indicated by arrow 316. Arrow 319 illustrates a direction extending perpendicularly away from a left side of the patient 310 and, in various embodiments, indicates a 270° rotational angle in a clockwise direction, or 90° rotational angle in a counter-clockwise direction, for angular movement of the insertion tube 315 with respect to the 0° reference angle indicated by arrow 316.

In an embodiment, referring again to FIG. 2A, each of the codes from the plurality of codes 207 marked on the surface of insertion tube 200 is indicative of a specific angle of rotation of the tube area marked by that code with respect to the direction of arrow 316 of FIG. 3B. As the endoscopic device is inserted and rotated inside a patient's body, the detector/reading unit 208 detects the codes 207 marked on the section of insertion tube 200 passing through its field of view 211 and records the same for further processing. For angular rotation, the codes 207 are placed at predefined positions, starting with a first position defined as the zero rotation angle point. As the codes 207 move from that zero rotation angle point, they indicate relative rotational angles.

The optical reader(s) of the detector/reading unit 208 records the codes 207 at different locations, indicative of insertion depth and relative position around the periphery, and tracks the locations, thereby being able to determine how many times, and in what direction, the endoscope insertion tube has moved. In embodiments, the system uses the information recorded by the detector unit 208 to calculate the exact angle of rotation of the endoscopic device with respect to the direction of arrow 316 in FIG. 3B.

In an embodiment, the system is configured such that, as the physician captures any image data, the main control unit 210 of the endoscope assembly maps the imaging data received from the viewing element 203 with the location information received from the processor 209 and tags the image with this location information. In an embodiment, the image data comprises stationary two dimensional images. In another embodiment, the image data comprises three dimensional images. In an alternate embodiment, the image data comprises a video of an interior portion of a body lumen captured for a specific time duration or a real time video. In all the above embodiments, the system stamps the image data with the location information received from the detector/reading unit 208. In some embodiments, the processor 209 is not present and the main control unit directly receives the location information from the reader 208 either through cables or through wireless communication.

In some embodiments, the plurality of codes 207 is etched on the surface of insertion tube 201 at the time of manufacturing of the endoscope assembly. In another embodiment, an independent strip or cover/skin comprising codes 207 is inserted or pasted on the insertion tube 200 either by the original equipment manufacturer or the user. The total length or specific sections of insertion tube 200 on which the codes 207 are marked may vary in different embodiments depending on the coding scheme. The exact nature and configuration of the detector/reading unit 208 mentioned in the above embodiments depends on the type of coding schemes used on the endoscopic device.

In some embodiments, the plurality of codes 207 has a uniform pattern across the length of the endoscopic device. However, in such a coding system, only relative measurement is possible, i.e. each set of codes within the plurality of codes 207 can be used to determine the relative change in position of the insertion device and not the insertion depth in absolute terms. To enable measurement of insertion depth in the absolute terms, in some embodiments, such as the embodiment shown in FIG. 2A, a non-uniform plurality of codes 207 is used in which the coding pattern varies across the length of the endoscopic device.

Figure 2B:
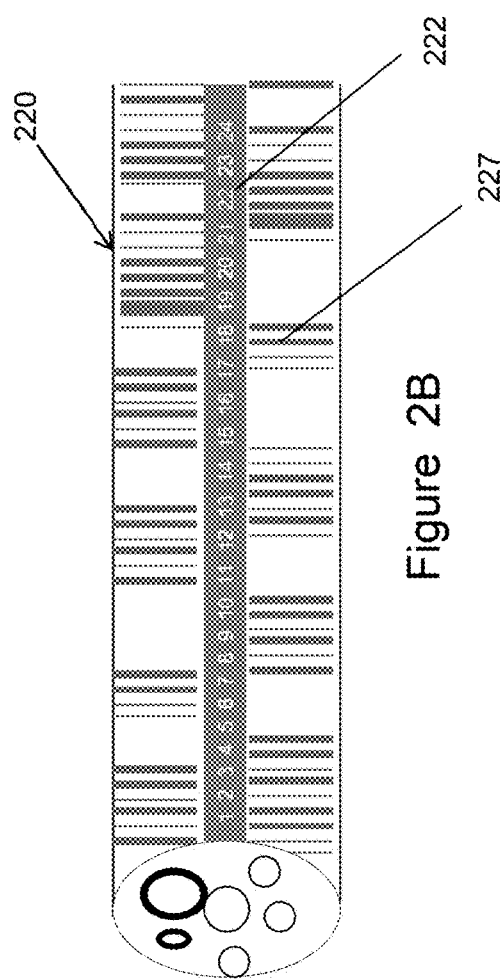
FIG. 2B illustrates a portion of an insertion tube comprising two dimensional barcode marks in accordance with an embodiment of the present specification.

In an embodiment, the plurality of codes 207 comprises simple linear barcodes and accordingly the detector/reading unit 208 comprises a simple optical device, such as a barcode reader. Reference is made to FIG. 2B showing an insertion tube 220 with a plurality of codes 227 marked over the outer surface of tube 220. In this coding scheme, the width of vertical lines and the spacing between alternate lines are used to define the longitudinal information and coding determined by the patterns of the lines is used to define the rotational information at any point. In another embodiment illustrated in FIG. 2C, two dimensional barcodes are used which comprise layers of a specific graphical pattern 247 marked over the outer surface of insertion tube 240. The encoding schemes comprising two dimensional barcodes provide a more advanced/detailed level of encoding that puts less load on the processor.

Figure 2C:
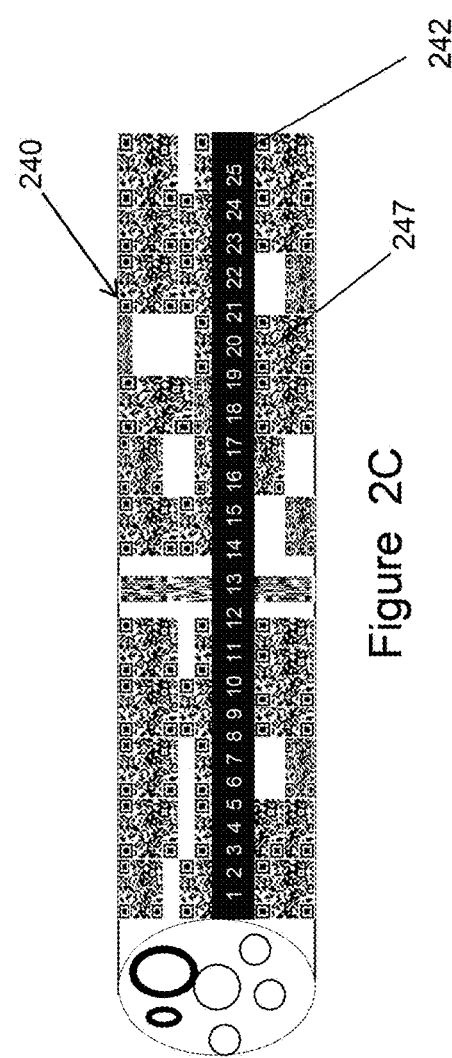
FIG. 2C illustrates a portion of an insertion tube comprising three dimensional barcode marks in accordance with an embodiment of the present specification.
Figure 2D:
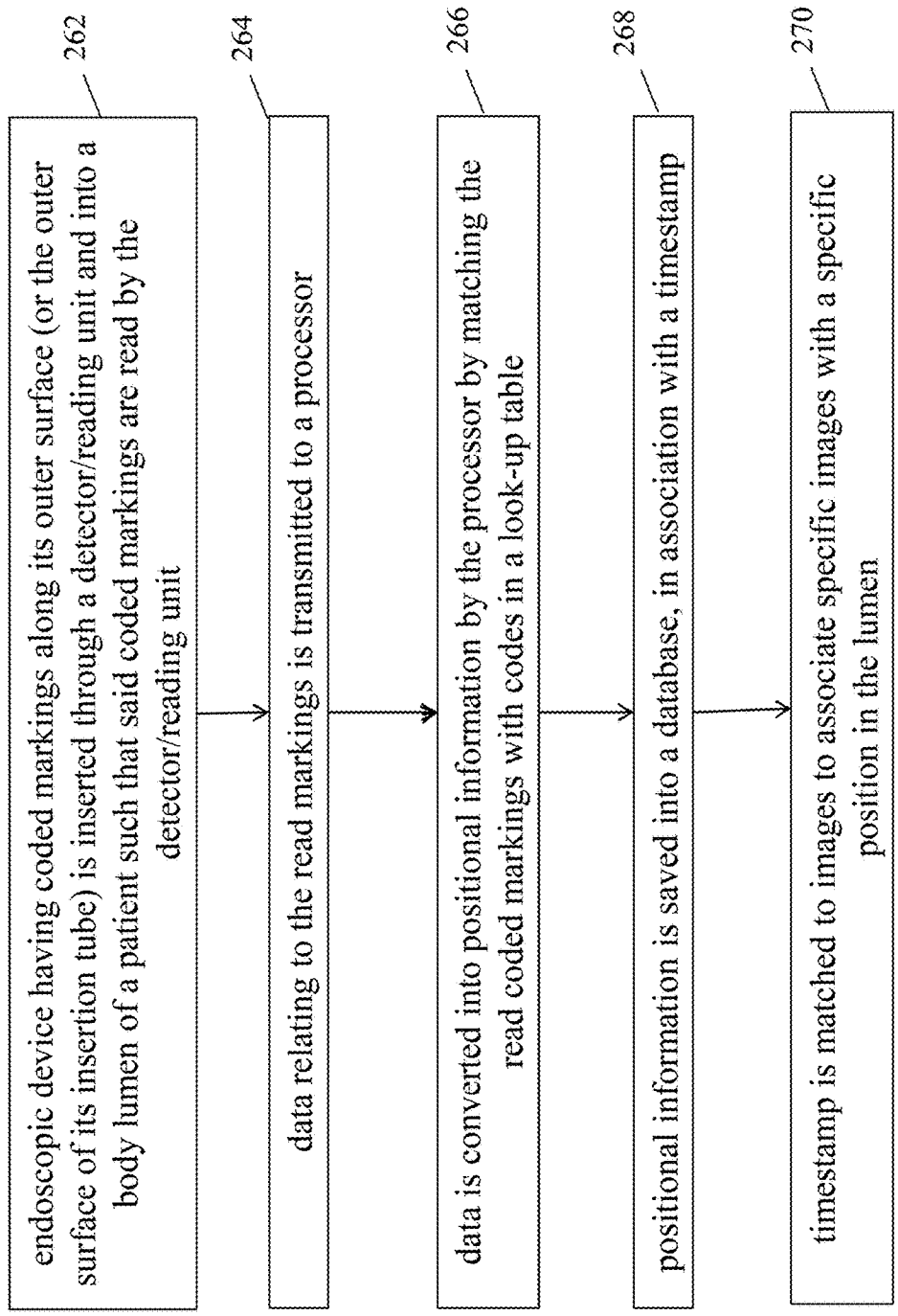
FIG. 2D is a flow chart listing the steps involved in a method of using an endoscopic device with coded markings and a detector/reading unit to determine position, in accordance with one embodiment of the present specification.

FIG. 2D is a flow chart listing the steps involved in a method of using an endoscopic device with coded markings and a detector/reading unit to determine position, in accordance with one embodiment of the present specification. At step 262, an endoscopic device having coded markings along its outer surface (or the outer surface of its insertion tube) is inserted through a detector/reading unit and into a body lumen of a patient such that said coded markings are read by detector/reading unit. Then, at step 264, data relating to the read markings is transmitted to a processor. The data is converted into positional information by the processor by matching the read coded markings with codes in a look-up table at step 266. The positional information is saved into a database, in association with a timestamp, at step 268. At step 270, the timestamp is matched to images to associate specific images with a specific position in the lumen. Therefore, images captured by the endoscopic device are tagged with a timestamp and the timestamp is used to associate the image with an insertion depth and direction of the endoscope.

In some embodiments of the present specification, such as the embodiments shown in FIGS. 2B and 2C, in addition to the coding system as described above, the insertion tube also comprises a conventional system of marking the insertion depth in numerical terms which may be physically inspected by the physicians. The strips 222, 242 in FIG. 2B and FIG. 2C respectively, contain information on the insertion depth in numerical terms which may be physically inspected by the physicians. Using a dual system as described in FIGS. 2B and 2C provides an alternative to the physicians in case they do not want to use the automatic location detection mechanism described in the present specification. In some embodiments, a similar strip comprising the information on the angular movement of the device is included across the circumference of the endoscopic device.

The exact resolution or the minimum unit of insertion depth and angular movement that can be measured depends on the coding scheme used for encoding the location information. Certain coding schemes, such as the two dimensional coding scheme mentioned in FIG. 2C, are more advanced and provide a higher level of resolution.

In an embodiment of the present specification, conventional number based markings are used both as codes to be automatically detected by a reader (for example, via computerized vision) and to enable backward compatibility by providing an option to the physicians to use a manual, visual inspection method for determining the insertion depth. The numbers represent the insertion depth at any position over the length of the insertion tube of the endoscope. A detector/reading unit, comprising an optical device such as a camera, is incorporated into the endoscopy system to capture images of the conventional numbers marked on the section of the insertion tube passing through the field of view of the detector/reading unit. In some embodiments, wherein the spacing between the numbers or marks is wide, a higher number of optical devices are required.

Figure 4:
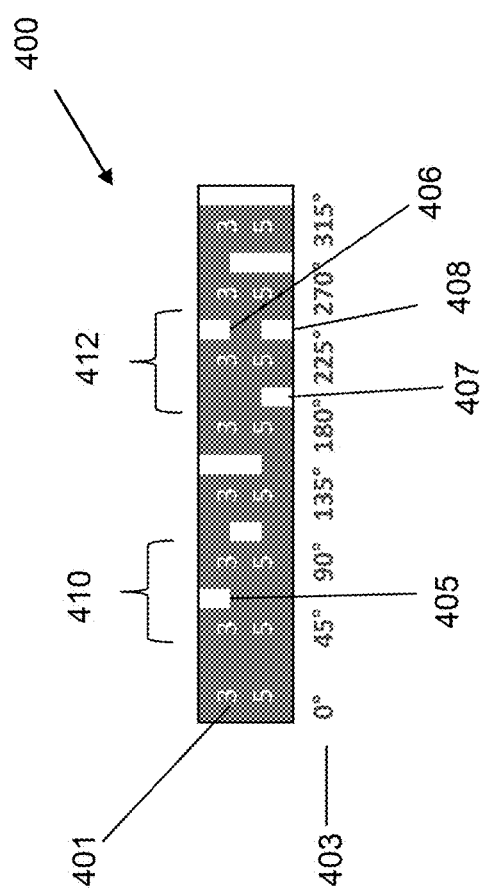
FIG. 4 is a snapshot of a number-based marking/coding scheme captured at a specific penetration depth of an endoscopic device, in accordance with one embodiment of the present specification.

In another embodiment of the present specification, an insertion tube of an endoscopic device includes number based codes/marks with narrow spacing between two alternate marks to reduce the processing load on the system and enhance the reliability of the location data estimation process. In this embodiment, the number of optical devices in the detector/reading unit is relatively low which reduces the system weight, cost and size. Reference is made to FIG. 4 which illustrates a number based sample marking/coding at a specific penetration depth.

The ribbon 400 depicted in FIG. 4 has been removed from an endoscope and spread out as a strip. In use, the ribbon 400 would be wrapped about a portion of an endoscope insertion tube corresponding to an insertion depth of 35 cm such that the numbers '35' could be read by a physician from all sides of the insertion tube. The ribbon 400 comprises numbers 401 which depict the insertion depth at the specified level of where the ribbon 400 would be placed on the insertion tube. In addition, the coding system comprises special marks/codes 405, 406, 407, 408 which are detected by the reader to determine the rotational angle 403 of the insertion tube. For example, in an embodiment, when a detector/reading unit has a field of view encompassing region 410, the detector/reading unit reads mark 405 and the system processes this information as a rotational angle of 67.5° (between 45° and 90°). When a detector/reading unit has a field of view encompassing region 412, the detector/reading unit reads marks 406, 407, 408 and the system processes this information as a rotational angle of 225°. In an embodiment, the physician can manually estimate the insertion depth and rotational angle by reading the number based codes at any level and by knowing a reference angle indicated by markings 402. In another embodiment, the optical reader automatically scans the images of the codes/marks of the section of insertion tube that passes through its field of view and uses this image information to decode the exact insertion depth and rotational angle with. In various embodiments, an embedded or independent processing unit configured for decoding the codes/marks calculates the exact insertion depth and rotational angle.

Positioning the Detector/Reading Unit in Colonoscopy Procedures

Figure 5A:
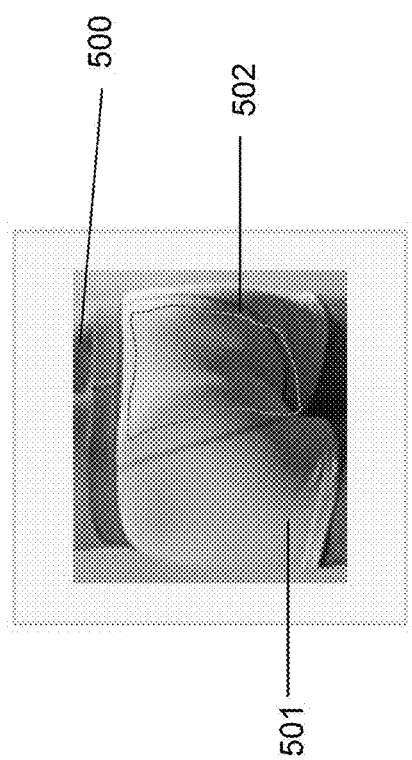
FIG. 5A illustrates an exemplary undergarment used in conjunction with colonoscopy procedures in accordance with an embodiment of the present specification.

One of ordinary skill in the art would appreciate that there may be multiple ways to position a detector/reading unit in the above embodiments without departing from the overall spirit and scope of this specification. In an embodiment, for example, in a colonoscopy procedure, the detector/reading unit is attached or fixed to a garment worn by the patient. In an embodiment, the garment comprises a special type of underwear designed for patients that protects the modesty of patients by limiting the areas of exposure during the procedure and at the same time allows implementing the novel system of location estimation disclosed in embodiments of the present specification. In an embodiment, the underwear comprises a section on the rear side which can be partially opened up and is adapted to receive and hold a detector/reading unit, such as an optical reader, such that the detector/reading unit is able to read the codes marked on an insertion tube as it is inserted into a patient's anus. Reference is made to FIG. 5A, which illustrates an undergarment 501, such as an underwear, configured to hold a detector/reading unit, in accordance with an embodiment of the present specification. As shown in FIG. 5A, a person 500 is shown wearing an undergarment 501. Section 502 depicts the portion of the undergarment 501 which is configured to be partially opened such that a physician can insert an endoscopic device into the patient's anus. In an embodiment, the undergarment 501 is also configured to securely hold a detector/reading unit in place as an endoscopic device is passed through the reader and advanced into a patient's anus. In an embodiment, the undergarment 501 comprises flaps or Velcro straps located at the interface between the free ends of section 502 and the remainder of the undergarment 501 which are used to secure section 502 when in a closed position. However, any other known methods of opening up and closing the portion comprising section 502 may be used in various embodiments of the present specification. In an embodiment, the undergarment 501 is made of a material such that it can be washed and disinfected after every use. In another embodiment, the undergarment 501 is fabricated from a disposable material and intended for single use.

The section 502 is large enough to enable a physician to conveniently manipulate the patient's buttocks to ease the insertion of the endoscope. In an embodiment, the section 502 comprises a plurality of flaps which can be opened up and, once the insertion stage is completed, the physician repositions the flaps to conceal the patient's buttocks as much as possible. Moreover, the physician at this stage attaches or fastens the detector/reading unit such, as an optical reader, to the patient's body or to the undergarment using straps, buckles, clamps or other similar fastening means. In some embodiments, the fastening means comprise part of the undergarment. In other embodiments, the fastening means comprise part of the detector/reading unit. In still other embodiments, complimentary fastening means are provided on both the undergarment and the detector/reading unit wherein said complimentary fastening means couple with one another to secure the detector/reading unit to the undergarment and, by extension, to the patient's body.

Figure 5B:
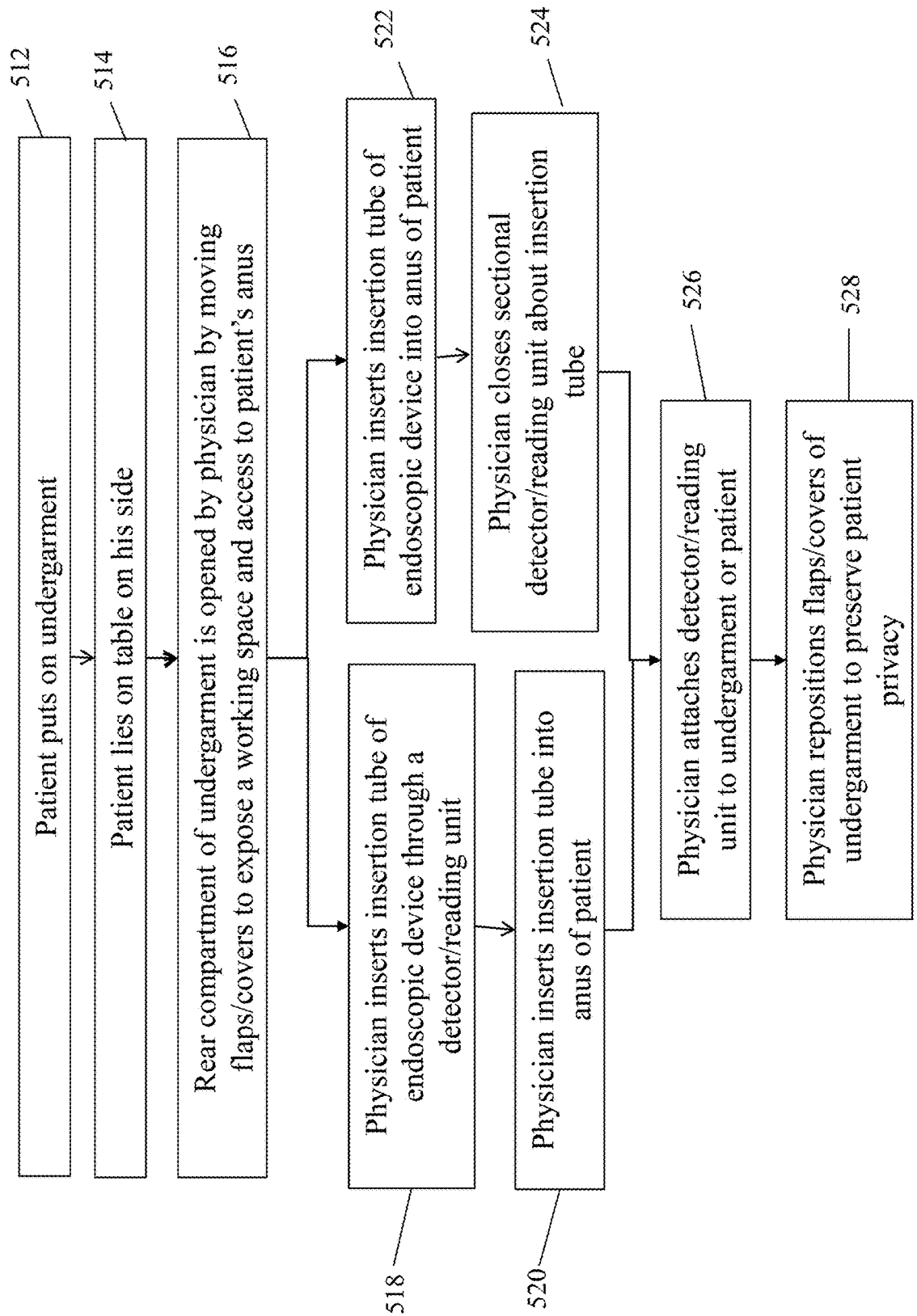
FIG. 5B is a flow chart listing the steps involved in various methods of securing a detector/reading unit to an undergarment and/or patient body, in accordance with some embodiments of the present specification.

FIG. 5B is a flow chart listing the steps involved in various methods of securing a detector/reading unit to an undergarment and/or patient body, in accordance with some embodiments of the present specification. At step 512, a patient puts on a specially designed undergarment in accordance with various embodiments of the present specification. The patient lies on a table on his side at step 514. Then, at step 516, a rear compartment of the undergarment is opened by the physician by moving flaps/covers on the rear side of the undergarment to expose a working space providing access to the patient's anus. In one embodiment, at step 518, the physician first inserts the insertion tube of an endoscopic device through a detector/reading unit. The physician then inserts the insertion tube into the anus of the patient at step 520. The detector/reading unit is then attached to the undergarment or to the patient at step 526. Optionally, the physician repositions the flaps/covers of the undergarment to preserve patient privacy at step 528. In another embodiment, following step 516, the physician first inserts the insertion tube of an endoscopic device into the anus of the patient at step 522. The physician then closes a sectional detector/reading unit about the insertion tube at step 524. The detector/reading unit is then attached to the undergarment or to the patient at step 526. Optionally, the physician repositions the flaps/covers of the undergarment to preserve patient privacy at step 528.

Figure 6A:
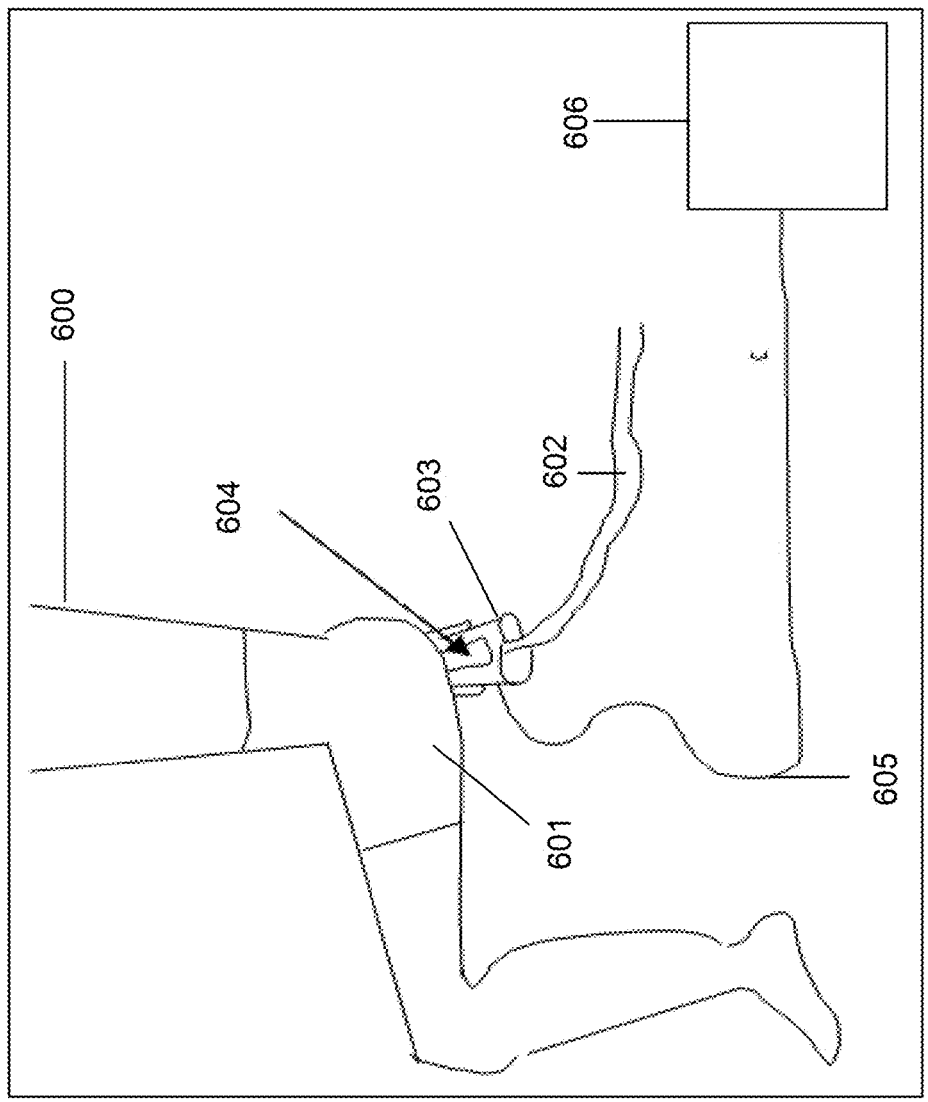
FIG. 6A illustrates a colonoscopy procedure performed on a patient using an endoscopic assembly in accordance with an embodiment of the present specification.

FIG. 6A illustrates a colonoscopy procedure performed on a patient using an endoscope assembly in accordance with an embodiment of the present specification. As shown in FIG. 6A, a patient 600 is shown wearing a specially designed underwear 601 which is adapted to partially open from the rear side to enable conducting a colonoscopy procedure. In an embodiment, the underwear 601 comprises flaps 604 which are lifted or positioned to open the rear side section of underwear 601 and enable the insertion of insertion tube 602 into the patient's 600 anus. In an embodiment, a detector/reading unit 603, such as an optical reader, is coupled to the patient body. In an embodiment, the underwear 601 comprises means to provide firm support to the detector/reading unit 603. In an embodiment, the detector/reading unit 603 is coupled to a main control unit 606 either wirelessly or through a wire 605 for power supply and data link.

Positioning the Detector/Reading Unit in Gastroscopy Procedures

Figure 6B:
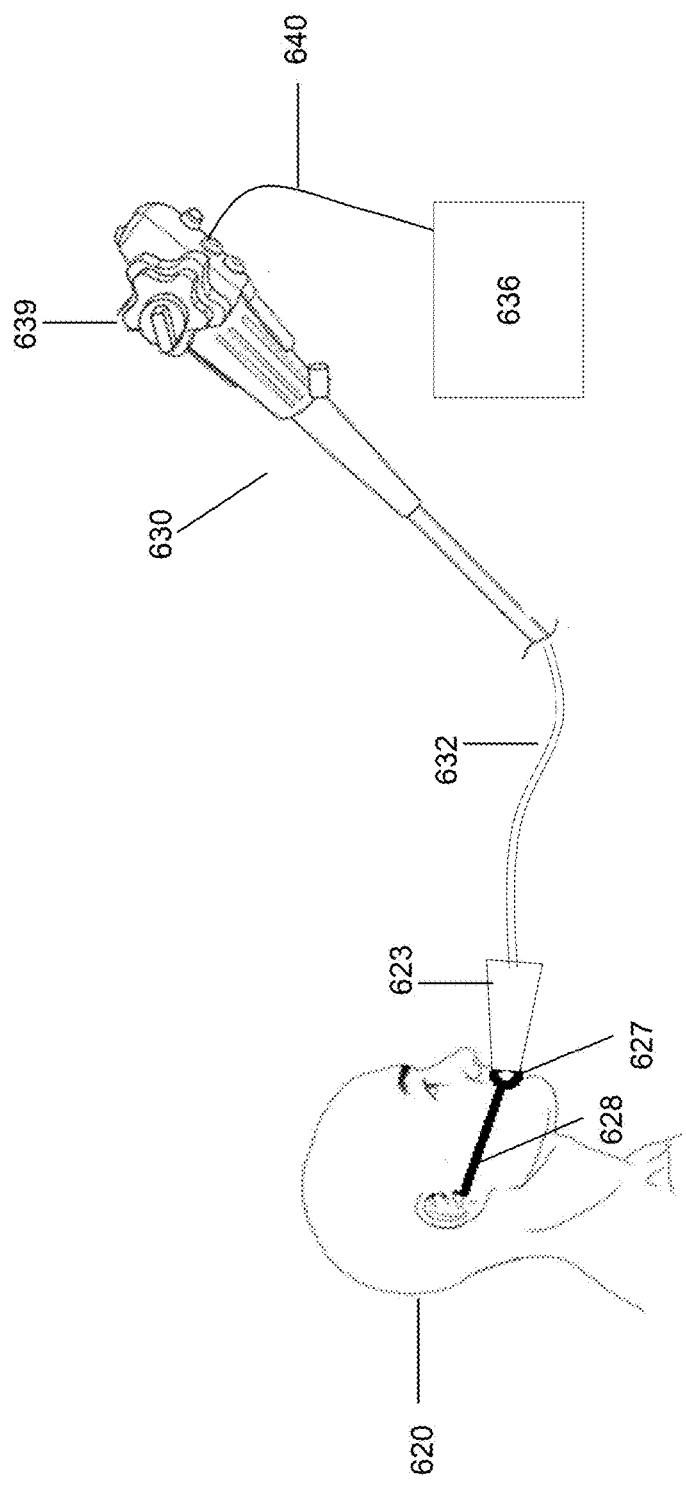
FIG. 6B illustrates a gastroscopy procedure performed on a patient using an endoscope assembly in accordance with an embodiment of the present specification.

FIG. 6B illustrates a gastroscopy procedure performed on a patient 620 using an endoscope assembly in accordance with an embodiment of the present specification. As shown in FIG. 6B, a patient 620 is shown wearing a mouthpiece 627 which is configured in a firm position around the patient's 620 mouth with the help of a band 628. In an embodiment, the mouthpiece 627 is similar to any conventional mouthpiece used for gastroscopy procedures. In another embodiment, the mouthpiece 627 is specially configured for the embodiments of the present specification wherein the mouthpiece 627 comprises a means to couple with a detector/reading unit 623 and hold it in a firm position during the procedure. In yet another embodiment, the mouthpiece 627 and detector/reading unit 623 comprises one unified unit. The endoscope 630 comprises a control handle 639 which is coupled to an insertion tube 632 and a main control unit 636 through a cord 640. In an embodiment, the physician inserts the insertion tube section 632 of the endoscopic device in the patient's 620 mouth through a central opening in the detector/reading unit 623 and performs the medical procedure. In embodiments, the detector/reading unit 623 comprises detection devices such as an optical reader(s) for detecting the location information of the device inside the patient's body and communicating the same to main control unit 636. In an embodiment, the detector/reading unit 623 is coupled to the main control unit 636 through a wire 640. In another embodiment, the detector/reading unit is coupled to the main control unit thorough a wireless link. In some embodiments, the detector/reading unit comprises batteries to meet its power requirements.

Figure 7:
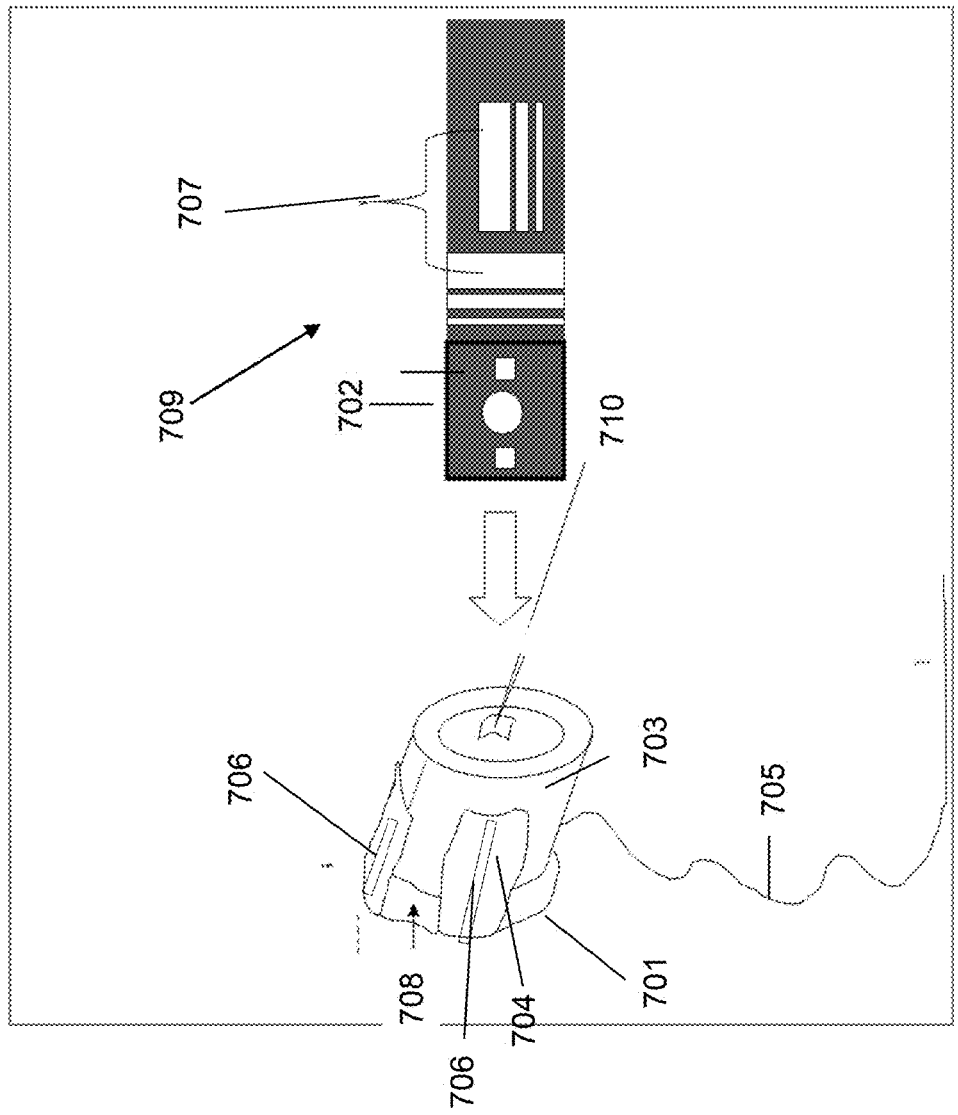
FIG. 7 illustrates an endoscope assembly comprising an endoscope, a detector/reading unit, and a specially designed undergarment, in accordance with an embodiment of the present specification.

FIG. 7 illustrates an endoscope assembly comprising an endoscope 709, a detector/reading unit 703, and a specially designed undergarment 701, in accordance with an embodiment of the present specification. As shown in FIG. 7, a specially designed patient underwear 701 is configured such that it can be opened from a rear side 708 to expose a section through which the colonoscopy procedure is to be performed. The rear portion 708 of the underwear 701 is configured such that it can be opened by opening or repositioning rear side covers or flaps 704. The exact number of flaps or covers 704 may vary in various embodiments. One of ordinary skill in the art would appreciate that there may be other alternative means to enable the partial opening of the rear side 708 of the underwear 701 without departing from the spirit and scope of the present specification. In some embodiments, buttons, buckles or zippers are used to close or open the rear side 708 of the underwear 701.

In some embodiments, the underwear 701 is adapted to provide support to hold the detector/reading unit 703 in a firm position. In some embodiments, the underwear 701 comprises additional structural elements 706, such as struts, buckles or chains, to provide support to the detector/reading unit 703. In an embodiment, the underwear 701 is configured such that the structural elements 706 comprise a housing to receive the detector/reading unit 703 which is adapted to hold the detector/reading unit 703 firmly in place.

As shown in FIG. 7, in an embodiment, the detector/reading unit 703 is structured in a hollow cylindrical shape such that the hollow portion of the cylinder allows the physician to insert medical tools through it and into the patient's body. In an embodiment, the inside portion of the cylindrical detector/reading unit 703 comprises a plurality of optical devices 710 for detecting the codes 707 marked on the endoscopic device 709 and for estimating the location information, comprising the insertion depth and rotational angle of the endoscopic device 709, based on said codes 707. In embodiments, the optical windows that cover the optical devices 710 are sealed and are resistant to water and other liquids such as intestine fluids and most of all, sterilizers and disinfectants. The exact relationship between the detector/reading unit 703 and the optical devices 710 is dependent on the type of markings/codes 707 and spacing between them.

In an embodiment, the detector/reading unit 703 comprises a monolithic structure. In another embodiment, the detector/reading unit 703 comprises a plurality of modular components which can be attached together to configure the detector/reading unit 703. In an embodiment, the detector comprises two semi-circular cylindrical sections which can be attached together with clamps. In an embodiment, the two semi-circular cylindrical sections are individual components and can be separated completely from one another. In another embodiment, the two semi-circular cylindrical sections are joined by a hinge and can be opened and closed about said hinge. In an embodiment, the physician first inserts the insertion tube 702 of the endoscopic device 709 in the patient's body and subsequently the two halves of the detector/reading unit 703 are attached around the insertion tube 702.

In one embodiment, the detector/reading unit 703 is an optical reader. However, in other embodiments, the detector/reading unit 703 comprises any other type of reading equipment, such as an RF reader. The exact configuration of the detector/reading unit 703 depends on the coding system used to encrypt the location information of the endoscopic device 709.

In an embodiment, the insertion tube 702 of the endoscope assembly is encrypted with codes 707, such as barcodes, which comprise information on the insertion depth and rotational angle of the endoscopic device 709 with respect to certain reference parameters. As the distal section of the insertion tube 702 is inserted into the patient's anus through the detector/reading unit 703, the optical devices 710 scan the codes 707 marked on the section of insertion tube 702 which are in the field of view of the optical devices 710. The optical devices 710 communicate the code 707 information to a processing unit which, based on specific algorithms, decrypts the location information comprising the insertion depth and rotational angle of the endoscopic device 709. In various embodiments, the processing unit transmits the information to a main control unit through a cable 705. In an embodiment, the cable 705 provides the power supply to the detector/reading unit 703. In another embodiment, the cable 705 provides a two way data link for configuring the detector/reading unit 703 and for transmitting the real time location data from the detector/reading unit 703 to the main control unit. In another embodiment, the processing function is performed by a processor located in the main control unit and the detector/reading unit 703 directly transmits the captured code 707 information to the main control unit. In other embodiments, no cable is included, all data communication is wireless, and the detector/reading unit 703 and optical devices 710 are battery powered.

In an embodiment, the optical devices 710 are configured to continuously scan the code 707 information to generate the location information in real time which is used to generate real time videos or three dimensional images by merging or fusing the two dimensional images which are simultaneously captured by the endoscopic device 709. In another embodiment, the optical devices 710 are configured to scan the code 707 information whenever a physician provides instruction to capture any image for stamping/tagging that specific image with its location information.

Three-Dimensional and Video Imaging

In another embodiment, the system generates a three dimensional image based on user instruction. In an embodiment, the physician first captures a first two dimensional image. Subsequently, the physician changes the position of the endoscopic device and captures a second two dimensional image. The physician then provides an instruction to the system, using a voice command or a button on the control handle, and the system recognizes that the first and the second two dimensional images correspond to a single 3D capture and applies image processing algorithms to merge the two images to generate a 3D image. In the process of merging a plurality of two dimensional images to create a three dimensional image or video, the system performs the steps of aligning the multiple images to a common rotational angle when the rotational angle is different between the different image captures. The system also aligns the brightness, contrast and chromaticity among the images to bring them to a standard platform.

For example, in one embodiment, a 3D image is captured on a side camera of an endoscope. The distal tip of the endoscope is straightened to point forwards as much as possible such that a pathological structure of interest lies within the side camera's FOV (Field Of View). A first 2D image is captured by the side camera. Tags for the first 2D image capture include a depth=81.4 cm and an angle=10.3°. A second 2D image is then captured by the same side camera after the endoscope has been moved. Tags for the second 2D image capture include a depth=82.1 cm and an angle=12.9°. The two 2D images are processed to obtain similar brightness and color. The first 2D image is shifted up in a number of lines respective with (12.9−10.3)/2=1.3°. This is related with the optic system's field of view. The second 2D image is shifted down the same number of lines.

The two images are now similar and aligned except they are taken at different endoscope depths. Knowing that the camera type is a side camera, the difference in depth is equivalent to the distance between two cameras placed on a same horizontal axis capturing a 3D image. This is similar to the way humans capture a 3D image using both eyes.

A software or firmware module constructs a single 3D image from the two 2D images in a way similar to that of the human brain. Distance of an object, or picture element, from the "cameras" is calculated by the difference in its horizontal positions in the two 2D images. The greater the difference between the two images, the shorter the distance. Similarly, a smaller difference means a greater distance. The equivalent horizontal distance between the positions of the side camera when the first and second 2D images are captured is known to the system. In this example, it is 82.1 cm−81.4 cm=0.7 cm.

In another example in accordance with embodiments of the present specification, a 3D image is captured on a front camera of an endoscope. The distal tip is straightened to point forwards as much as possible such that a pathological structure of interest lies within the front camera's FOV (Field Of View). A first 2D image is captured by the front camera. Tags for the first 2D image capture include a depth=92.5 cm and an angle=12.3°. A second 2D image is then captured by the front camera after the endoscope has been moved. Tags for the second 2D image capture include a depth=91.7 cm and an angle=13.4°. The two 2D images are processed to obtain similar brightness and color. The first 2D image is rotated clockwise (13.4−12.3)/2=0.55°. The second 2D image is rotated counterclockwise 0.55°. The two images are now similar and aligned except they are taken at different endoscope depths.

A software or firmware module constructs a single 3D image from the two 2D images. Distance of an object, or picture element, from the camera is calculated by the difference in its size (diameter/circumference/area) in the two 2D images. The greater the difference between the two images, the shorter the distance. Similarly, a smaller difference means a greater distance. The equivalent distance between the positions of the front camera when the first and second 2D images are captured is known to the system. In this example, it is 92.5 cm–91.7 cm=0.8 cm.

In embodiments, various parameters, such as the type of coding scheme and the spacing between codes, influence the selection of type and number of optical devices required in the detector/reading unit, such as detector/reading unit 703 of FIG. 7. In embodiments, the selection is also based on the primary requirement that, at all times, the field of view of at least one optical device should encompass a code or any other type of marking on the device.

In various embodiments, the length of the detector/reading unit 703 varies between 5-12 cm and the inner diameter of the detector/reading unit 703 varies between 5-8 cm. One of ordinary skill in the art would appreciate that the above ranges are mentioned just for exemplary purpose and one can configure a reader unit with other suitable dimensions without departing from the spirit and scope of this specification.

The use of a long and narrow device such as detector/reading unit 703 also prevents the random spray of fecal matter in all directions in case the patient suddenly has a bowel movement. Such matter shall be contained within the cylindrical structure or may be sprayed as a narrow cone. With this feature, physicians can avoid using accessories such as masks and goggles. It is more convenient for the physicians to conduct procedures without such accessories and also the image quality seen by physicians will be better in case they are not wearing goggles.

In an embodiment, the underwear 701 is designed such that it can be used as a standalone piece of equipment which the patients can wear to protect their modesty even if the location detection is not performed and the corresponding location detector/reading unit 703 is not attached to the patient.

Conical Detector/Reading Unit

Figure 8:
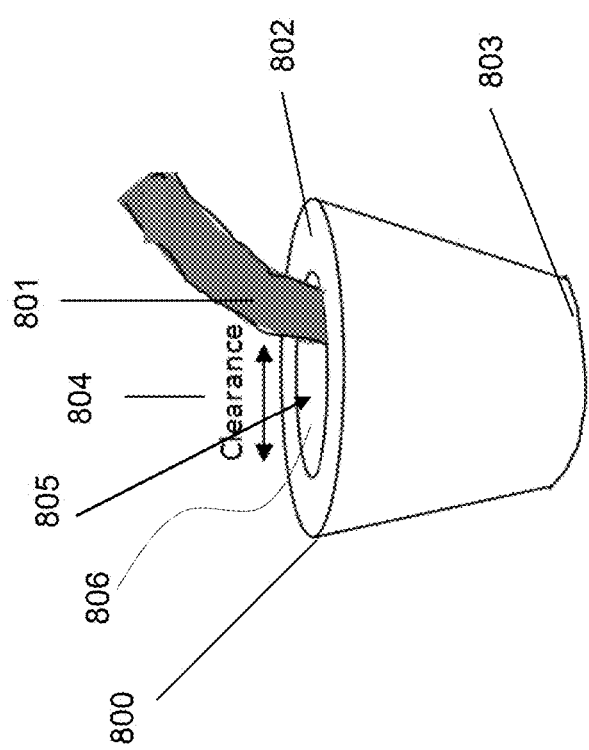
FIG. 8 illustrates an alternative embodiment of a detector/reading unit in the form of a truncated hollow conical structure, in accordance with one embodiment of the present specification.

FIG. 8 illustrates an alternate embodiment of a detector/reading unit 800 in the form of a truncated hollow conical structure. A hollow portion or opening 805 in the center of the truncated cone allows the physician to insert medical tools therethrough and into a patient's body lumen. The inside surface 806 of the conical detector/reading unit 800 comprises a plurality of optical devices to read codes marked on medical tools, such as insertion tube 801 of an endoscopic device, for establishing the location information of such a device. In embodiments, the detector/reading unit 800 is structured such that during a procedure, the radius of its proximal end 802 positioned towards the physician is greater than the radius of its distal end 803 positioned towards the patient. In various embodiments, the inner and outer diameters of the detector/reading unit 800 at its distal end 803 are in ranges of 3-5 cm and 4-6 cm respectively. In various embodiments, the inner and outer diameters of the detector/reading unit at its proximal end 802 are in ranges of 5-7 cm and 6-8 cm respectively. Such a conical structure includes greater clearance 804 at the proximal end 802 which provides increased maneuverability for the physician while operating the endoscopic device as compared to operating with a detector/reading unit having a cylindrical structure of uniform radius. The conical structure is further superior to the cylindrical structure as it minimizes friction between the insertion tube 801 of the endoscope and the detector/reading unit 800 which could wear out the endoscope's outer skin or markings. Further, a conical unit is more convenient for physicians as the potential friction between the endoscope and a cylindrical detector/reading unit may strain the physician, requiring him to apply extra force for longitudinal or rotational motion.

Ring-Shaped Detector/Reading Unit

Figure 9:
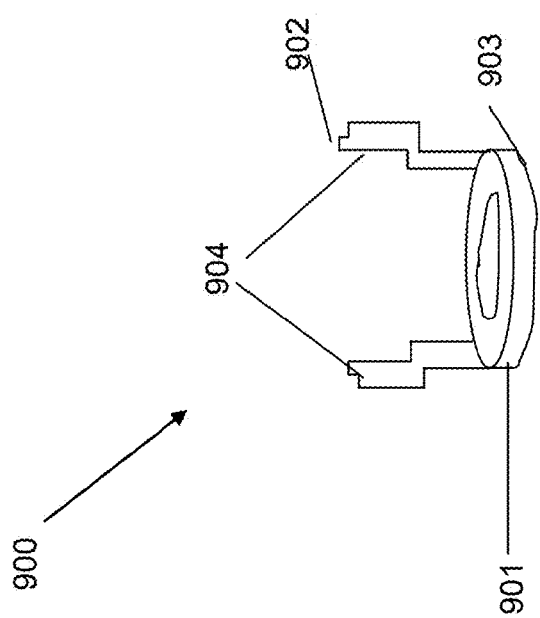
FIG. 9 illustrates an alternate embodiment of a detector/reading unit comprising a ring shaped base unit.

FIG. 9 illustrates an alternate embodiment of a detector/reading unit 900 comprising a ring shaped base unit 901. As shown in FIG. 9, the detector/reading unit 900 comprises a ring shaped base unit 901 which is adapted to firmly attach or couple to the body of a patient either directly or with the assistance of a garment, such as underwear, designed for this purpose and described in this specification. A set of arms 904 extend proximally from the base unit 901 and comprise the reading devices, such as optical devices, embedded therein. When in use, the base unit 901, at the distal end 903 of the detector/reading unit 900, is positioned toward the patient and the arms 904, at the proximal end 902 of the detector/reading unit 900, are positioned toward the physician. The configuration described in FIG. 9 offers the benefit of lighter weight as compared to the cylindrical shaped and conical shaped detector/reading units described in FIG. 7 and FIG. 8 respectively, while the cylindrical and conical shaped detector/reading units offer higher structural stability.

Pathological Structure Size Determination

Figure 10:
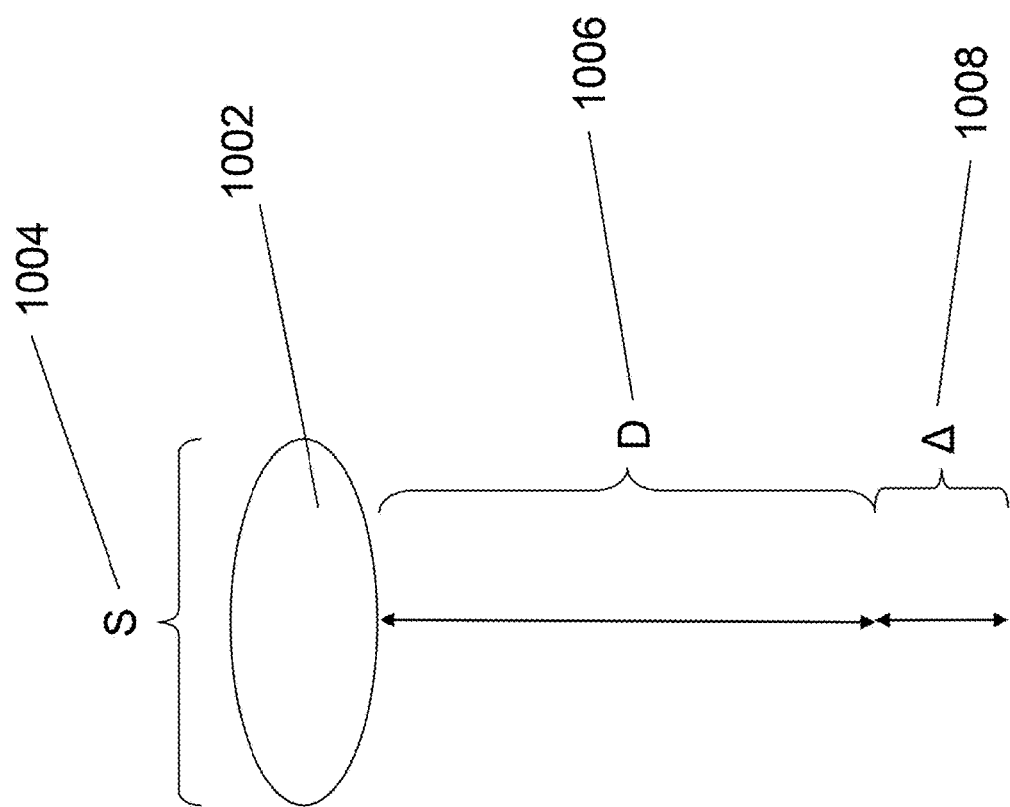
FIG. 10 illustrates a set of distances used to calculate the size of a pathological structure viewed by an endoscopy system in accordance with one embodiment of the present specification.

In an embodiment of the present specification, the size of a pathological structure, such as a polyp or any other abnormality, can be measured using the location information corresponding to various captured images of the said pathological structure. Referring to FIG. 10, a mathematical method to calculate the size is described wherein:

S 1004=Actual size of Pathological Structure 1002;
D 1006=Distance to the pathological structure 1002 in a first image;
Δ 1008=Difference is insertion depth between two consecutive images (obtained from a detector/reading unit);
D 1006+Δ 1008=Distance to the pathological structure 1002 in a second image;
Pxl1=the size in pixels of pathological structure 1002 when the endoscope's distance is D 1006;
Pxl2=the size in pixels of the pathological structure 1002, when the endoscope's distance is D 1006+Δ 1008;
tg=tangent;
$tg^{-1}$=arctangent; and
K=a factor translating from angular field of view to number of pixels.

Then:

$$Pxl1 = 2Ktg^{-1}\frac{S}{2D};$$

$$Pxl2 = 2Ktg^{-1}\frac{S}{2(D+\Delta)}$$

And so both D and S can now be extracted:

$$D = \Delta\frac{tg(Pxl2/2K)}{tg(Pxl1/2K) - tg(Pxl2/2K)}$$

$$S = 2Dtg(pxl1/2K)$$

Therefore S, the size of a pathological structure, is a function of: the endoscope's distance D, the pixel size of the structure at distance D, and the factor K. As described above, the size S 1004 of the pathological structure 1002 is deduced from the size in pixels of said pathological structure 1002 captured in two different image shots at insertions whose depth difference is known.

Real Time Image Mapping in Endoscopic Procedures

Figure 11:
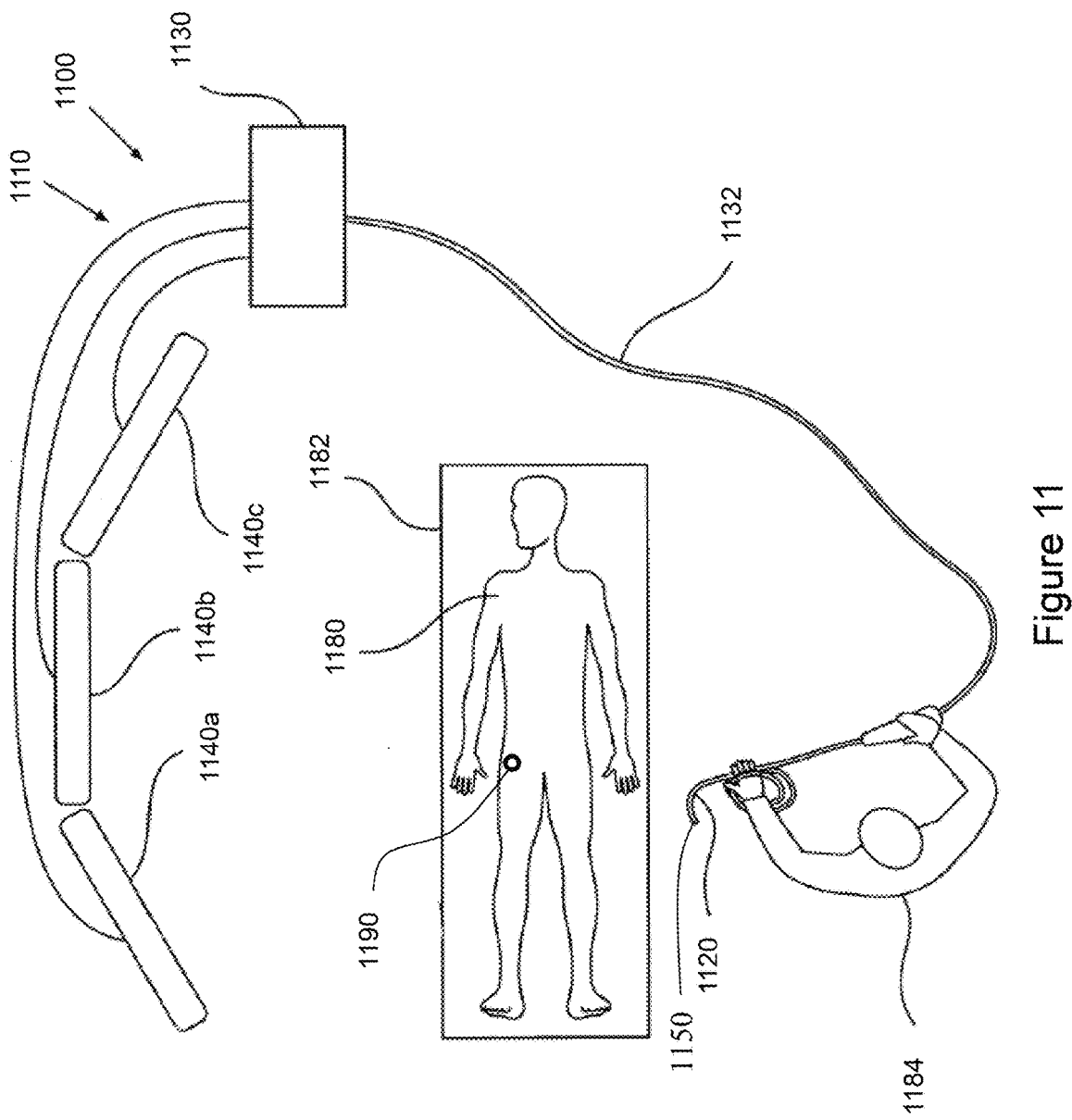
FIG. 11 illustrates a physician and patient and an endoscopy system in accordance with one embodiment of the present specification.

FIG. 11 illustrates a physician and patient and an endoscopy system in accordance with one embodiment of the present specification. The figure schematically depicts a layout of an endoscopy system 1110 and an associated interface unit 1100 deployed in an operation room, according to some embodiments. A patient 1180 is supported on a bed 1182 and a physician 1184 employs an endoscope 1120 of endoscopy system 1110 during a medical procedure.

The endoscope 1120 is connected to a main controller 1130 by a utility cable 1132. In embodiments, the endoscope 1120 provides three simultaneous endoscopic views using three viewing elements housed in a distal tip 1150 of endoscope 1120. In embodiments, the main controller 1130 is connected to three display screens, 1140a, 1140b, and 1140c. In an embodiment, each display screen is configured to display a corresponding view of the three endoscopic views provided by endoscopy system 1110, as described above. In an embodiment, the main controller 1130 is connected to at least one display configured to display a corresponding view of the three endoscopic views provided by endoscopy system 1110.

In embodiments, a first sensor (not shown) is mounted in distal tip 1150 of the endoscope 1120. In an embodiment, the first sensor comprises a transmitter/transceiver and a second sensor or base unit is located on or proximal to endoscope 1120 such that it remains outside the body cavity where endoscope 1120 is inserted. In embodiments, the second sensor is placed on the body of the patient 1180 such as at location 1190 on the surface of patient's 1180 body. Location 1190 may be a location near an opening on the patient 1180 body from where endoscope 1120 is inserted, such as the patient's rectum. In another embodiment, the second sensor 1190 is placed at a pre-defined location on a bed 1182 of the patient 1180 undergoing the endoscopic scan. In this case, the patient 1180 may be stably secured to the bed 1182. In another embodiment, the second sensor 1190 is placed at a pre-defined location on a flexible tube of endoscope 1120 between its handle and the body of the patient 1180. In embodiments, the second sensor 1190 includes a receiver/transceiver that communicates with the first sensor.

In an embodiment, the first sensor senses a location of the endoscope tip within the lumen and transmits the same in real time to the second sensor 1190. In embodiments, the first sensor captures image information in three dimensions, and also records the time of image capture. The first sensor transmits image, time, location and any other information to second sensor 1190 by using wireless signals lying in the sub-Giga hertz frequency field. In an embodiment, both sensors use frequencies below 1 gigahertz and within ranges such as 30-1000 MHz, 30-150 MHz, 150-1000 MHz, or any other range authorized for medical uses. The received endoscope tip location information is processed using a continuous signal stream to provide a map of the scanned portions of the lumen in real time. In an embodiment, the map is displayed on one or more display screens coupled with endoscope 1120. In various embodiments, both sensors are of any suitable type, such as accelerometers, gyro devices and radar.

Also, in an embodiment, the first sensor functions as a navigation unit that sends real time endoscope-tip navigation information to second sensor 1190 that functions as a base unit. In an embodiment, the second sensor 1190 provides a reference plane for obtaining a real time position of the distal tip of endoscope 1120. A pre-defined algorithm may be used to process the reference plane obtained from sensor 1190 and the navigation co-ordinates obtained from the first sensor to provide a location of the endoscope tip in real time. In embodiments, the real-time location information is provided within a rectangular range of 0.1-3 mm and 0.1-1 mm. The rectangular accuracy of the obtained position depends upon a frequency of navigation co-ordinates received from the first sensor.

In an embodiment, sensor 1190 is only a transceiver to provide a reference plane for obtaining a real time position of the distal tip of endoscope 1120. In another embodiment, the first sensor is a radar based sensor for capturing a current location of the endoscope tip and transmitting this information to sensor 1190.

Figure 12:
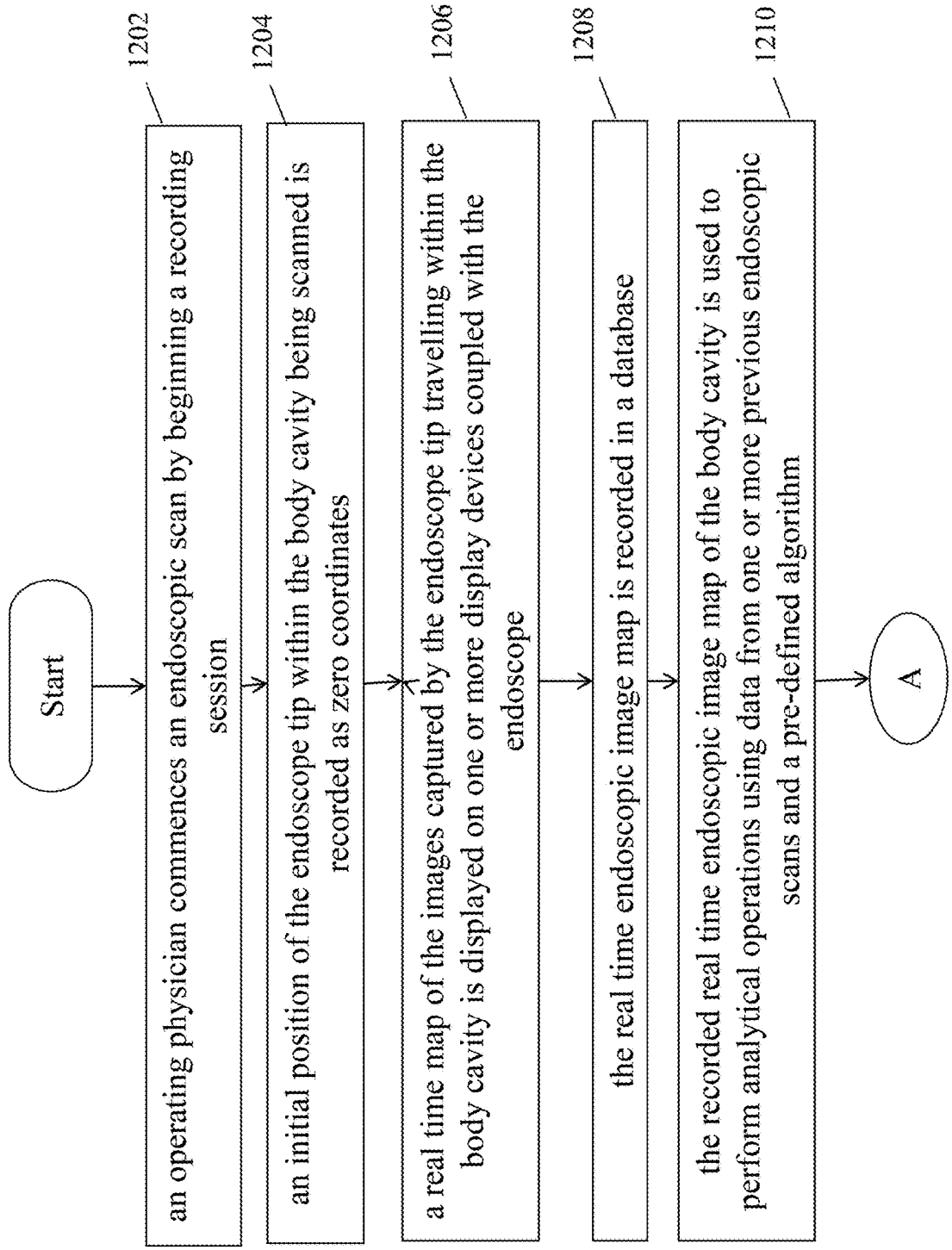
FIG. 12 is a flowchart illustrating a method of obtaining a real time image map of an endoscope tip from within a body cavity during an endoscopic procedure, in accordance with an embodiment of the present specification.

FIG. 12 is a flowchart illustrating a method of obtaining and using a real time image map of an endoscope tip from within a body cavity during an endoscopic procedure, in accordance with an embodiment of the present specification.

At step 1202, an operating physician commences an endoscopic scan by beginning a recording session. In an embodiment, a time synch operation is also performed at the commencement of the endoscopic scan. In an embodiment, a recording session is started by pressing a button provided on a handle portion of the endoscope immediately before inserting the endoscope tip into a body cavity. In other embodiments, the recording session is started by operating any pre-defined control. In various embodiments, once the recording session begins, internal images of the scanned body cavity captured by the imaging elements positioned in the endoscope tip are recorded in a predefined format in a specified database.

At step 1204, an initial position of the endoscope tip within the body cavity being scanned is recorded as zero coordinates. At step 1206, a real time map of the images captured by the endoscope tip travelling within the body cavity is displayed on one or more display devices coupled with the endoscope. The image map is drawn by using the zero coordinates as an initial reference point. U.S. patent application Ser. No. 14/697,933, entitled "System and Method of Scanning a Body Cavity Using a Multiple Viewing Elements Endoscope" and filed on Apr. 28, 2015, describes one method for mapping images of a body cavity captured by an endoscope in real time onto a reference image and is herein incorporated by reference in its entirety. U.S. patent application Ser. Nos. 14/505,387 and 14/505,389, both entitled "Endoscope with Integrated Sensors" and filed on Oct. 2, 2014, are also herein incorporated by reference in their entirety.

At step 1208, the real time endoscopic image map is recorded in a database. At step 1210, the recorded real time endoscopic image map of the body cavity is used to perform analytical operations using data from one or more previous endoscopic scans and a pre-defined algorithm. In an embodiment, a pace of the endoscope tip scanning the lumen is also displayed and recorded by using information from steps 1206-1208 to calculate a difference between two subsequent endoscope tip positions.

At step 1212, the operating physician marks one or more regions of interest on the endoscopic image of the body cavity being displayed in real time on one or more display devices, the regions of interest being related to observation of an abnormality. In an embodiment, the operating physician also records one or more comments related to the observed abnormality with respect to the marked regions. In an embodiment, a plurality of formats and colors are made available for marking the regions of interest and recording corresponding remarks. In an embodiment, an operating physician also records audio comments corresponding to a marked region.

At step 1214, if during the endoscopic scan, the endoscope tip arrives at a particular location within the body cavity which was marked during an endoscopic scan performed at an earlier time, an audio and/or visual alert is displayed. In various embodiments, the alert is generated and triggered when the sensor tip location is recorded and, in real-time, compared against saved marked locations from prior scans wherein said saved locations are associated with a region of interest. A user can load the previous record and display it synchronously with a live procedure. This is achieved with the time and position information collected by the first sensor at the distal tip of the endoscope. The user or operating physician is alerted and he may consult the endoscopic map of the same body cavity captured and recorded at an earlier time in order to compare and/or assess the condition of an observed abnormality. In an embodiment, the endoscopic image map captured at an earlier time is displayed in a portion of the display screen displaying the real time image map.

In an embodiment, the endoscopic image map captured at an earlier time is displayed at the same pace at which the endoscope tip is scanning the lumen at a current time. Hence, the speed of a video displaying an endoscopic image map captured at an earlier time (dependent upon the speed at which the endoscope was traversing a body lumen) is adjusted to be in synch with the speed at which the operating physician moves the endoscope distal tip within the lumen in the current procedure, enabling the physician to compare the images captured at different times. In an embodiment, assuming an insertion depth X in a current endoscopy procedure, the displayed reference image frame will be the closest one related to depth X. This is to allow the physician to compare identical sections of the lumen between two procedures separated in time (reference and current). An insertion speed at point X in the reference endoscopic procedure is defined as Vr and a current procedure insertion speed at the same point X is defined as Vc. When Vc<Vr, the rate of pulling frames from the reference will be slower than the frame rate sent to display screens. This means some of reference frames would be duplicated when sent to the display screens. When Vc>Vr, the rate of pulling frames from the reference will be faster than the frame rate sent to display screens. This means some of the reference frames would be skipped when sent to the display screens.

At step 1216, an extraction of the endoscope tip from within the body cavity signals an end of the recording session. In an embodiment, the operating physician is required to operate a control (such as pressing a button provided on the endoscope) in order to stop the recording session, whereas in another embodiment, the extraction of endoscope tip from within the body cavity automatically stops the recording session. In various embodiments, automatic cessation of recording occurs as soon as the detector/reading unit can no longer detect markings on the insertion tube. In other words, recording automatically stops once the insertion tube has been removed from the reader such that there are no markings for the detector/reading unit to detect. The operating physician can re-insert the endoscope tip into the body cavity to begin a new recording session. Once a recording session ends, an updated endoscopic image map is displayed on one or more display devices coupled with the endoscope.

In an embodiment, the present specification provides a system and method for transmitting images and videos of endoscopic procedures to a plurality of devices by using wireless network technology. In an embodiment, a main control unit of the endoscope is provided with a wireless module that establishes a link over wireless platforms such as IEEE 802.11ac or IEEE 802.11ad which are used for transmitting live video of endoscopic procedures in formats such as 1080p at a frequency of 59.94 Hz. In an embodiment, live videos of endoscopic procedures are displayed on one or more display devices connected via the wireless link to the endoscope's main control unit.

In an embodiment, one or more portable devices such as but not limited to cell phones, tablets, laptops, and other illustrative devices such as three dimensional demonstration, 3D holography, present in the vicinity of the endoscope being used to perform a patient's scan are used to perform functions such as live broadcast of the endoscopic scan, database searches to obtain a required patient's scan results and compare them with one or more scan results. Further, in an embodiment, a mobile application may be provided to be used in conjunction with a wireless module installed in a main control unit of the endoscope and one or more mobile devices to enable the operating staff, such as nurses, to obtain all of a patient's endoscopic scan data stored in a predefined database along with a live video of a current on-going scan. In an embodiment, the mobile application provides functionalities such as zooming in and scrolling through the endoscopic scan data displayed on a mobile device.

In an embodiment, a wireless module installed within a main control unit of the endoscope is connected to a secured Internet service which is used to obtain software/firmware updates for the main control unit. In an embodiment, the software/firmware updates are obtained via a push data method wherein the updates can be downloaded and installed automatically whenever the main control unit is connected to the secured Internet link, or be programmed to check for updates at pre-defined intervals. In an embodiment, a message indicating an available update is displayed on a screen of the main control unit, enabling a user to choose to proceed with the update. Also, in various embodiments, a status of the main control unit does not change during an endoscopic procedure. Any updates/changes to software/firmware of the main control unit take place only when the endoscope is not being used for scanning a patient body.

In an embodiment, the wireless module and the secured Internet link is also used for performing maintenance activities on the control unit by transmitting required diagnostic applications and software/firmware updates, without having to send support personnel to the endoscope's location.

In an embodiment, a wireless module installed within a main control unit of the endoscope connected to a secured internet service is used by an operating physician to consult in real time with one or more doctors present at separate geographical locations regarding an ongoing endoscopic procedure via audio/textual methods. A video coverage of the procedure is transmitted to one or more doctors at remote locations in real time along with the operating physician's queries. This feature of the present specification enables an operating physician to take help from a plurality of doctors present at remote locations during an endoscopic procedure for improving the diagnostic quality of the procedure.

In an embodiment, a recording of an endoscopic procedure is made in real time by using the wireless module installed within the main control unit. The recording serves as a back-up record of the procedure and is stored in one or more databases. The recorded procedures stored in databases can be used at a later date for patient treatment as well as for education and training purposes. In an embodiment, every recorded procedure is synchronized to a pre-defined clock time by a qualified professional.

In an embodiment, in addition to a wireless module installed within the main control unit, one or more Wi-Fi modules are also installed in other parts of an endoscope, such as the endoscope handle. In such a scenario where multiple Wi-Fi modules are installed at multiple positions on the endoscope, the precise location of the endoscope tip within a patient's body is obtained by correlating the location information received via each Wi-Fi module.

Video Processing Architecture

Figure 13:
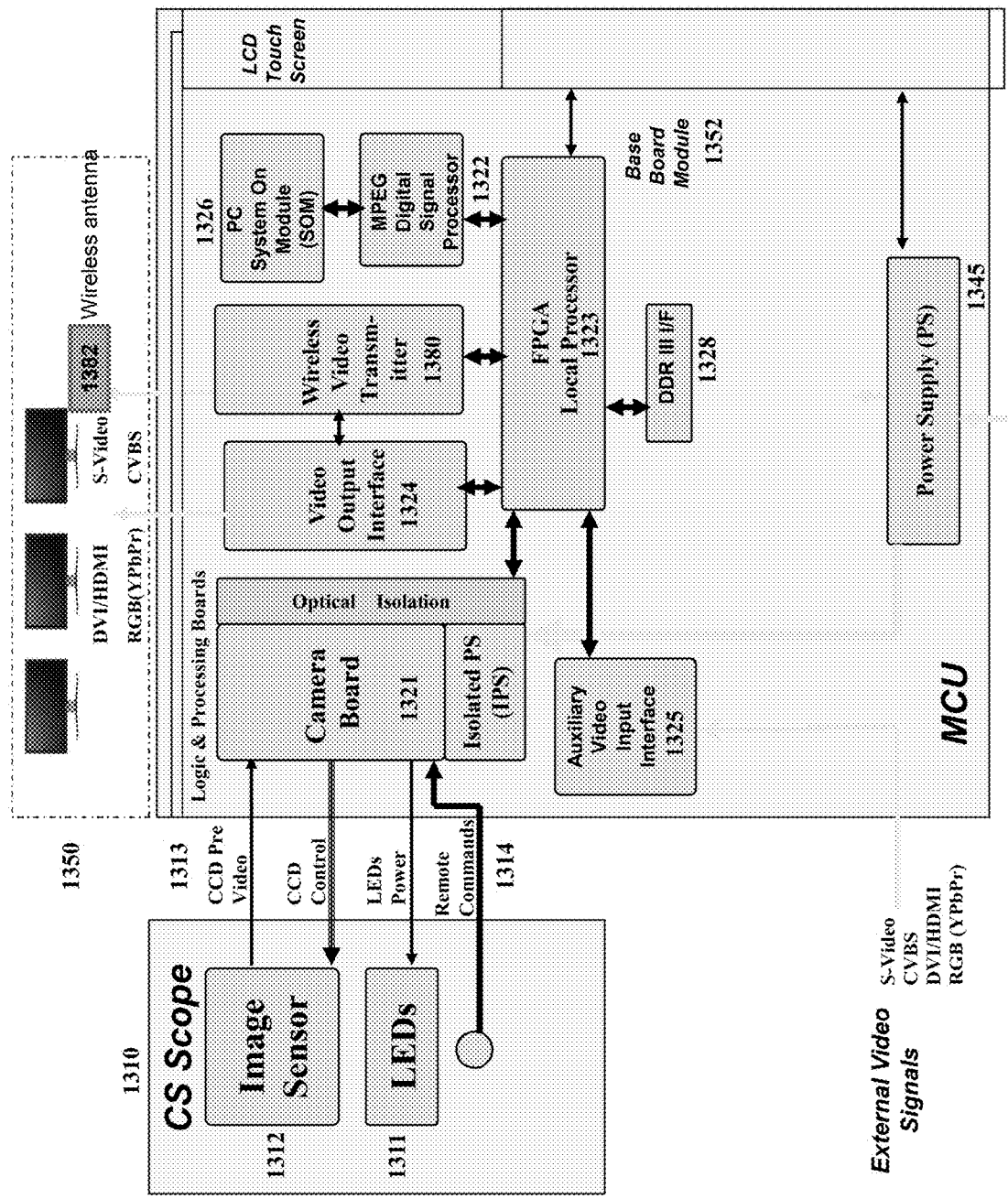
FIG. 13 is a block diagram illustrating an exemplary video processing architecture, according to an embodiment of the present specification.

FIG. 13 is a block diagram illustrating an exemplary video processing architecture, according to an embodiment of the present specification. FIG. 13 details how a video controller 1320 containing a controller circuit board (Base Board Module) 1352 of a main control unit (1130 of FIG. 11) operatively connects with an endoscope 1310 and display units 1350. Referring to FIG. 13, the video controller 1320 (which contains controller circuit board 1352) comprises a camera board 1321 that controls the power supplies to LEDs 1311, transmits controls for the operation of image sensor(s) 1312 (comprising one or more cameras) in the endoscope, and converts pre-video signals from image sensors to standard video signals. The image sensor(s) 1312 may be a charge coupled device (CCD) or a complementary metal oxide semiconductor (CMOS) imager. The camera board 1321 receives pre-video signal(s) 1313 generated by the CCD imager and also other remote commands 1314 from endoscope 1310. In one embodiment, PC 1326 is connected directly to FPGA 1323 and not through MPEG 1322, which is an optional component.

Video Controller 1320 further comprises elements for processing the video obtained from the image sensors 1312 through camera board 1321, as well as other elements for system monitoring and control.

All these elements are connected with a Base Board Module 1352, which is a printed circuit board (PCB). In an embodiment, elements such as ICs (Integrated Circuits) are connected by soldering, an element 1326 (SOM or System on Module) is connected by mounting, while all other elements are connected by means of cables.

In some embodiments, receiving the optical information (line coding, bar codes) or RFID, as described in various embodiments of the present specification, is performed through a USB connection with the main control unit (1130 of FIG. 11). In various embodiments, processing of the positional information is performed jointly by the FPGA 1323, PC system on module 1326, and a GPU of the main control unit. In one embodiment, a plurality of codes on the insertion tube of an endoscopic device comprises numbers representing the insertion depth at any position over the length of the insertion tube. The detector/reading unit contains one or more optical devices (i.e. cameras) for detecting the printed numbers. The video carrying the images of said printed numbers is processed by the PC system on module 1326, FPGA 1323, and system GPU, by means of computerized vision, to establish the depth of insertion. Display information regarding the position of the endoscope is displayed similarly to any other on screen display (OSD) or graphic overlay type.

Various elements on Base Board Module 1352 are described as follows:

FPGA (Field Programmable Gate Array) 1323:

FPGA 1323 is a logic device programmed specifically for the system requirements and performs tasks that may be categorized by two types: logic tasks which are implemented by hardware (i.e. should not or must not be implemented by software), and logic tasks related to video image processing. In an embodiment, the Base Board Module 1352 includes one or more double data rate type three synchronous dynamic random access memory modules (DDR3) 1328 in communication with FPGA 1323.

Among logic tasks related to video image processing, FPGA 1323 generates an internal test pattern that may be provided to video outputs via a Video Output Interface 1324 to multiple display units 1350. In embodiments, a wireless video transmitter 1380 is connected to the FPGA 1323 and the video output interface 1324. In an embodiment, the transmitter 1380 is configured to wirelessly transmit video output to wireless receivers among display units 1350, through a wireless antenna 1382. In various embodiments, the Base Board Module 1352 includes one or more wireless video transmitters 1380. For example, in some embodiments, wherein the endoscope 1310 is a gastroscope, the Base Board Module 1352 includes one or two wireless video transmitters 1380. In another embodiment, wherein the endoscope is a colonoscope, the Base Board Module 1352 includes three wireless video transmitters 1380. In another embodiment, the endoscope comprises P cameras, M transmitters, and N screens, where each of M, N, and P are different natural numbers. Where there are additional transmitters than cameras, the additional transmitters may transmit placeholder, screen saver, or other generic display information.

In an embodiment, a wireless transmitter 1380 installed within the main control unit of the endoscope is connected to a secured Internet service which may be used to obtain software/firmware updates for the main control unit. In an embodiment, the software/firmware updates are obtained via a push data method wherein the updates can be downloaded and installed automatically whenever the main control unit is connected to the secured Internet link, or be programmed to check for updates at pre-defined intervals. In an embodiment, a message indicating an available update is displayed on a screen of the main control unit, enabling a user to choose to proceed with the update. Also, in various embodiments, a status of the main control unit does not change during an endoscopic procedure. Any updates/changes to software/firmware of the main control unit take place only when the endoscope is not being used for scanning a patient body.

In an embodiment, the wireless module, including transmitter 1380 and the secured Internet link may also be used for performing maintenance activities on the control unit by transmitting required diagnostic applications and software/firmware updates, without having to send support personnel to the endoscope's location.

In an embodiment, the wireless module installed within a main control unit of the endoscope connected to a secured internet service may be used by an operating physician to consult in real time with one or more doctors present at separate geographical locations regarding an ongoing endoscopic procedure via audio/textual methods. A video coverage of the procedure may be transmitted to one or more doctors at remote locations in real time along with the operating physician's queries. This feature of the present specification enables an operating physician to take help from a plurality of doctors present at remote locations during an endoscopic procedure for improving the diagnostic quality of the procedure.

In an embodiment, a recording of an endoscopic procedure is done in real time by using the wireless module installed within the main control unit. The recording may serve as a back-up record of the procedure and may also be stored in one or more databases. The recorded procedures stored in databases may be used at a later date for patient treatment as well as for education and training purposes. In an embodiment, every recorded procedure is synchronized to a clock time pre-defined by a qualified professional.

In an embodiment, in addition to a wireless module installed within the main control unit, one or more Wi-Fi modules are also installed in other parts of an endoscope, such as the endoscope handle. In such a scenario where multiple Wi-Fi modules are installed at multiple positions on the endoscope, the precise location of the endoscope tip within a patient's body is obtained by correlating the location information received via each Wi-Fi module.

DSP (Digital Signal Processor) 1322:

DSP 1322 is used for recording compressed (coded) video and playing back decompressed (decoded) video. In an embodiment, the standard of compressed video is H264 or equivalent (such as MPEG). In another embodiment, the video controller 1320 does not include a digital signal processor and the PC system on module 1326 communicates directly with the FPGA 1323.

Operationally, the FPGA 1323 selects for DSP 1322, the desired video to be recorded, i.e. any of the inputs, or, more likely, a copy of one or more of the screens. In the latter case, this includes the OSD and format conversion. In the likely case of the screen's format differing from that of DSP's 1322 required video input format, the FPGA 1323 also converts the screen's format to the desired DSP 1322 format while transmitting video to DSP 1322.

Auxiliary Video Input Interface 1325:

In an embodiment, the video input to the Auxiliary Video Input Interface 1325 comprises analog video, such as in CVBS (color, video, blanking, sync), S-Video or $YP_BP_R$ format or digital video (DVI), and may be displayed as such.

SOM (System on Module) 1326:

SOM 1326 provides an interface to input devices such as keyboard, mouse, and touchscreen via a Touch I/F. Through these input devices, together with the buttons in a Front Panel, the user controls the system's functionality and operational parameters. In an embodiment, a peripheral component interconnect express (PCIe) bus connects SOM 1326 with FPGA 1323. Most common types of data traffic over the PCIe may include:

a. SOM 1326 to FPGA 1323: Commands (for example, when the user changes operational parameters); and b. FPGA 1323 to SOM 1326: Registers values, which provide an indication of the internal status, and captured images.

Other Functionalities:

Video Controller 1320 further controls one or more fluid, liquid and/or suction pump(s) which supply corresponding functionalities to the endoscope through a pneumatic I/F, pump and check valve. Video Controller 1320 further comprises an on-board power supply 1345 and a front panel which provides operational buttons for the user.

Camera board 1321 receives video signal 1313 which, in an embodiment, comprises three video feeds, corresponding to video pickups by three endoscopic tip viewing elements (one front and two side-looking viewing elements), as generated by image sensors 1312. In an embodiment, the three video feed pickups, corresponding to the three viewing elements (the front-looking, left-side looking and right-side looking viewing elements) of an endoscopic tip (such as the three viewing elements of the tip section 150 of FIG. 1B), are displayed on three respective monitors.

In an embodiment, display units 1350 includes one or more portable devices, such as but not limited to, cell phones, tablets, laptops, and other illustrative devices such as three dimensions demonstration, 3D holography, present in the vicinity of the endoscope being used to perform a patient's scan. Display devices, such as those including wireless receivers/transceivers, are used to perform functions such as live broadcast of the endoscopic scan, database searches to obtain a required patient's scan results and compare them with one or more scan results, etc.

Further, in an embodiment, a mobile application is provided to be used in conjunction with a wireless module installed in a main control unit of the endoscope and one or more mobile devices to enable operating staff, such as nurses, to obtain all of a patient's endoscopic scan data stored in a predefined database along with a live video of a current on-going scan. The mobile application provides functionalities such as zooming in and scrolling through the endoscopic scan data displayed on a mobile device.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An endoscope assembly comprising:
an endoscope comprising:
 a control handle configured to control one or more functions of the endoscope;
 an insertion tube having a length extending distally from said control handle and comprising a plurality of markings; and
 at least one imaging assembly at a tip section of the insertion tube configured to generate two-dimensional image data of a plurality of areas in a field of view of the at least one imaging assembly, and to transmit the two-dimensional image data to a processor; and
a reading unit configured to detect said plurality of markings during insertion of the insertion tube into a subject, and to transmit data representative of said plurality of markings to the processor; and
a main control unit coupled to said control handle and comprising said processor, wherein said processor is adapted to merge the transmitted two-dimensional image data, based on the transmitted data representative of said plurality of markings, to generate three-dimensional image data of the areas viewed by the at least one imaging assembly.

2. The endoscope assembly of claim 1, wherein the at least one imaging assembly includes a plurality of imaging assemblies.

3. The endoscope assembly of claim 1, wherein the reading unit is adapted to surround a portion of the length of the insertion tube and remain outside of the control handle.

4. The endoscope assembly of claim 1, wherein the reading unit is configured to detect rotation of the insertion tube about the central longitudinal axis of the insertion tube.

5. The endoscope assembly of claim 1, wherein the processor is adapted to use the data representative of the plurality of markings to calculate location information related to the location of the endoscope, wherein the two-dimensional image data includes a plurality of image frames, and wherein the processor is adapted to stamp each image frame with the location information.

6. The endoscope assembly of claim 4, wherein the two-dimensional image data includes a first image frame and a second image frame; wherein the processor is adapted to store a rotation angle associated with each of the first image frame and the second image frame; wherein the first image frame has a rotation angle different from the rotation angle of the second image frame; wherein the processor is configured to align the first image frame and the second image frame to a common rotation angle.

7. The endoscope assembly of claim 1, wherein the three-dimensional image data includes a plurality of image frames; wherein the processor is adapted to align the brightness, contrast, and chromaticity among the plurality of image frames.

8. The endoscope assembly of claim 1, wherein the three-dimensional image data includes a plurality of image frames; wherein the processor is adapted to map the plurality of image frames in a pre-defined reference frame.

9. An endoscope assembly comprising:
an endoscope comprising:
a control handle configured to control one or more functions of the endoscope;
an insertion tube having a length extending distally from said control handle and comprising a plurality of markings; and
an imaging assembly at a tip section of the insertion tube configured to generate a plurality of two-dimensional image frames of a plurality of areas in a field of view of the imaging assembly, and to transmit the plurality of two-dimensional image frames to a processor, wherein the plurality of two-dimensional image frames includes a first two-dimensional image frame including a pathological structure at a first distance from the imaging assembly and a second two-dimensional image frame including the pathological structure at a second distance from the imaging assembly, wherein the first distance is different from the second distance; and
a reading unit configured to detect said plurality of markings during insertion of the insertion tube into a subject, and to transmit data representative of said plurality of markings to the processor; and
a main control unit coupled to said control handle and comprising said processor, wherein said processor is adapted to calculate a size of the pathological structure based on the transmitted data representative of said plurality of markings, the first two-dimensional image frame, and the second two-dimensional image frame.

10. The endoscope assembly of claim 9, wherein the imaging assembly includes a plurality of imaging assemblies.

11. The endoscope assembly of claim 9, wherein the reading unit is adapted to surround a portion of the length of the insertion tube and remain outside of the control handle.

12. The endoscope assembly of claim 9, wherein the reading unit is configured to detect rotation of the insertion tube about the central longitudinal axis of the insertion tube.

13. The endoscope assembly of claim 12, wherein the processor is adapted to store a rotation angle associated with each of the first two-dimensional image frame and the second two-dimensional image frame; wherein the first two-dimensional image frame has a rotation angle different from a rotation angle of the second two-dimensional image frame; wherein the processor is configured to align the first two-dimensional image frame and the second two-dimensional image frame to a common rotation angle.

14. The endoscope assembly of claim 9, wherein the processor is adapted to use the data representative of the plurality of markings to calculate location information related to the location of the endoscope, and wherein the processor is adapted to stamp the first two-dimensional image frame and the second two-dimensional image frame with the location information.

15. The endoscope assembly of claim 9, wherein the processor is adapted to align the brightness, contrast, and chromaticity among the plurality of two-dimensional image frames.

16. The endoscope assembly of claim 9, wherein the processor is adapted to map the plurality of two-dimensional image frames in a pre-defined reference frame.

17. The endoscope assembly of claim 9, wherein said processor is adapted to merge the transmitted plurality of two-dimensional image frames, based on the transmitted data representative of said plurality of markings, to generate three-dimensional image data of the areas viewed by the imaging assembly.

18. An endoscope assembly comprising:
an endoscope comprising:
a control handle configured to control one or more functions of the endoscope;
a display screen;
an insertion tube having a length extending distally from said control handle and comprising a plurality of markings; and
at least one imaging assembly at a tip section of the insertion tube configured to generate two-dimensional image data of a plurality of areas in a field of view of the at least one imaging assembly, and to transmit the two-dimensional image data to a processor; and
a reading unit configured to detect said plurality of markings during insertion of the insertion tube into a subject, and to transmit data representative of said plurality of markings to the processor; and
a main control unit coupled to said control handle and comprising said processor, wherein said processor is adapted to merge the transmitted two-dimensional image data, based on the transmitted data representative of said plurality of markings, to generate three-dimensional image data of the areas viewed by the at least one imaging assembly, wherein the three-dimensional image data includes a plurality of image frames, and wherein the processor is adapted to map the plurality of image frames in a reference frame.

19. The endoscope assembly of claim 18, wherein the display screen is configured to display the reference frame in a portion of the display screen.

20. The endoscope assembly of claim 18, wherein the at least one imaging assembly includes a plurality of imaging assemblies.

* * * * *